(12) United States Patent  (10) Patent No.: US 7,300,934 B2
Gabriel et al.  (45) Date of Patent: Nov. 27, 2007

(54) BENZAMIDE NITRILES

(75) Inventors: Tobias Gabriel, San Francisco, CA (US); Nancy Elisabeth Krauss, Mountain View, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 504 days.

(21) Appl. No.: 10/858,041

(22) Filed: Jun. 1, 2004

(65) Prior Publication Data

US 2004/0248949 A1    Dec. 9, 2004

Related U.S. Application Data

(60) Provisional application No. 60/475,296, filed on Jun. 2, 2003.

(51) Int. Cl.
- *A61K 31/495* (2006.01)
- *A61K 31/40* (2006.01)
- *A61K 31/497* (2006.01)
- *C07C 233/00* (2006.01)
- *C07D 333/22* (2006.01)

(52) U.S. Cl. ............ 514/249; 514/427; 514/343; 514/254.01; 514/254.02; 564/155; 549/77; 549/371.17; 544/58.7; 544/58.2; 544/163; 548/557; 548/187; 548/265.8

(58) Field of Classification Search ........ 564/155; 549/77, 493, 371.17; 548/557, 338.1, 371.7, 548/187, 265.8; 514/427, 249, 254.01, 254.02, 514/343; 544/58.7, 58.2, 163; 546/330
See application file for complete search history.

(56) References Cited

U.S. PATENT DOCUMENTS 6,462,076 B2 * 10/2002 Gabriel et al. ............ 514/463

FOREIGN PATENT DOCUMENTS

| DE | 44 00 749 A1 | 7/1995 |
|---|---|---|
| DE | 195 48 825 A1 | 7/1997 |
| WO | WO 01/96285 A1 | 12/2001 |

OTHER PUBLICATIONS

Hcaplus 115:45068.*
Hcaplus 136:53544.*

* cited by examiner

*Primary Examiner*—Thurman K. Page
*Assistant Examiner*—Binta Robinson
(74) *Attorney, Agent, or Firm*—Robert C. Hall

(57) ABSTRACT

Compounds of the formula (I)

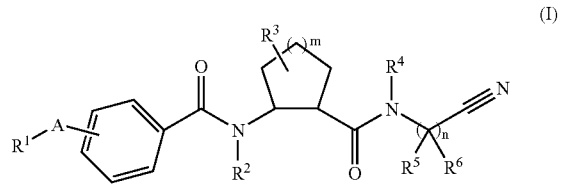

wherein m, n, A, $R^1$, $R^2$, $R^3$, $R^4$, $R^5$ and $R^6$ are as described herein, together with methods for making the compounds and using the compounds for treatment of diseases or conditions mediated by Cathepsin K.

66 Claims, No Drawings

BENZAMIDE NITRILES

CROSS-REFERENCE

This application claims the benefit of priority of U.S. Provisional Patent Application Ser. No. 60/475,296, filed Jun. 2, 2003, which is incorporated herein by reference in its entirety.

BACKGROUND OF THE INVENTION

Cysteine proteases have been viewed as lysosomal mediators of terminal protein degradation. Several newly discovered members of this enzyme class, however, are regulated proteases with limited tissue expression, which implies specific roles in cellular physiology and thus would allow a specific targeting of these activities without interfering with the general lysosomal protein degradation. Development of inhibitors of specific cysteine proteases promises to provide new drugs for modifying immunity, osteoporosis, neurodegeneration, chronic inflammation, cancer and malaria (Brömme, Drug News Perspect 1999, 12(2), 73-82; Chapman et al., Annu. Rev. Phys. 1997, 59, 63-88).

Cysteine proteases can be grouped into two superfamilies: the family of enzymes related to interleukin 1β converting enzyme (ICE), and the papain superfamily of cysteine proteases. Presently there are at least 12 human proteases of the papain family from which sequences have been obtained (cathepsin B, L, H, S, O, K, C, W, F, V(L2), Z(X) and bleomycin hydrolase). Cathepsin K was first discovered as a cDNA prominent in rabbit osteoclasts and referred to as OC-2 (Tezuka et al., J. Biol. Chem. 1994, 269, 1106-1109). Recent observations indicate that cathepsin K is the most potent mammalian elastase yet described. Cathepsin K, as well as cathepsins S and L, are also potent collagenases and gelatinases. Macrophages appear capable of mobilizing the active proteases within endosomal and/or lysosomal compartments to the cell surface under special circumstances. In this case, the cell surface/substrate interface becomes a compartment from which endogenous inhibitors are excluded and can be viewed as a physiological extension of the lysosome. This type of physiology is an innate trait of osteoclasts, a bone macrophage, and may also be exploited by other macrophages or cells in the context of inflammation. The abundance of cathepsin K in osteoclasts leads to the suggestion that cathepsin K plays an important role in bone resorption. Studies revealed that cathepsin K is the predominant cysteine protease in osteoclasts and is specifically expressed in human osteoclasts. A correlation between inhibition of cysteine protease activity and bone resorption has been reported (Lerner et al., J. Bone Min. Res. 1992, 7, 433; Everts et al., J. Cell. Physiol. 1992, 150, 221). Cathepsin K has been detected in synovial fibroblasts of RA patients, as well as in mouse hypertrophic chondrocytes (Hummel et al., J. Rheumatol. 1998, 25(10), 1887-1894.). Both results indicate a direct role of cathepsin K in cartilage erosion. P. Libby (Libby et al., J. Chin. Invest. 1998, 102 (3), 576-583) reported that normal arteries contain little or no cathepsin K or S whereas macrophages in atheroma contained abundant immunoreactive cathepsins K and S. Most of the elastolytic activity of tissue extracts associated with human atheroma compared to non-atherosclerotic arteries could be inhibited with E64, a non-selective cysteine protease inhibitor.

Tumor progression and metastasis are characterized by the invasion of tumors into adjacent tissues as well as by the dissociation of cancer cells from primary tumors and the infiltration of metastatic cells into organs. These processes are associated with the degragation of extracellular matrix proteins and thus require proteolytic activity. Cathepsin K has been identified in primary breast tumors, as well as in breast tumor-derived bone metastasis (Littlewood-Evans et al., Cancer Res. 1997, 57, 5386-5390), and prostate cancer (Brubaker et al., Journal of Bone and Mineral Research 2003, 18(2), 222-230.

Different classes of compounds, such as aldehydes, alpha-ketocarbonyl compounds, halomethyl ketones, diazomethyl ketones, (acyloxy)methyl ketones, ketomethylsulfonium salts, epoxy succinyl compounds, vinyl sulfones, aminoketones, and hydrazides have been identified as cysteine protease inhibitors (Schirmeister et al., Chem. Rev. 1997, 97, 133-171; Veber et al., Proc. Natl. Acad. Sci. USA 1997, 94, 14249-14254). The shortcomings these compounds suffer from include lack of selectivity, poor solubility, rapid plasma clearance and cytotoxicity. A need therefore exists for novel inhibitors useful in treating diseases caused by pathological levels of proteases, especially cycsteine proteases, including cathepsins, especially cathepsin K.

SUMMARY OF THE INVENTION

The present invention relates to novel benzamide nitrile derivatives, their manufacture and use as medicaments. In particular, the invention relates to novel nitriles of general formula (I)

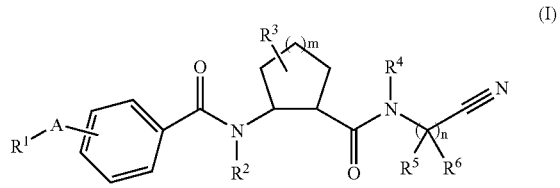

wherein:

m is from 1 to 3;

n is 1 or 2;

A is: $-(CR^aR^b[[_2]])_p-$; $-O-(CR^aR^b[[_2]])_s-$, $-NR^c-(CR^aR^b[[_2]])_t-$; or $-CH=CH-$;

wherein p and s each individually is from 0 to 3, t is from 1 to 3, and $R^a$, $R^b$ and $R^c$ each independently is hydrogen or alkyl;

$R^1$ is: halo; alkyl; alkenyl; alkoxy; hydroxy; amino; aryl; heteroaryl; heterocyclyl; $-S(O)_q-R^d$; $-NR^dS(O)_q-R^e$; or $-S(O)_q-NR^dR^e$ wherein q is from 0 to 2, $R^d$ is hydrogen, alkyl or optionally substituted phenyl and $R^e$ is hydrogen, alkyl, or pyridinylmethyl;

$R^2$, $R^3$, $R^4$ and $R^5$ each independently is hydrogen or alkyl; and $R^6$ is hydrogen, alkyl, optionally substituted benzyl, thienylmethyl, pyridylmethyl, cycloalkyl, or $-(CR^fR^g)_TS(O)_q-R^h$ where $R^f$, $R^g$ and $R^h$ each independently is hydrogen or alkyl and n is from 0 to 2;

with the proviso that when $R^1$ is halo or optionally substituted phenyl, $R^6$ is optionally substituted benzyl, thienylmethyl, pyridylmethyl, or $-(CR^fR^g)_TS(O)_q-R^h$; and pharmaceutically acceptable salts, solvents or prodrugs thereof.

DETAILED DESCRIPTION OF THE INVENTION

The compounds of the invention have an inhibitory activity on cysteine proteases, more particularly on systeine proteases of the papain superfamily, even more particularly on cysteine proteases of the cathepsin family, most particularly on cathepsin K. It was surprisingly found that this inhibiting effect on cathepsin K is selective with respect to other cathepsins. While compounds of general formula (I) very efficiently inhibit cathepsin K, the inhibition of other protease inhibitors such as cathepsin S, cathepsin L and cathepsin B is much weaker. Therefore the new compounds of general formula (I) are useful for specifically inhibiting cathepsin K. They can accordingly be used for the treatment of disorders which are associated with cysteine proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease. Accordingly, the present invention relates to a method for the prophylactic and/or therapeutic treatment of diseases which are associated with cysteine proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease, which method comprises administering a compound of formula (I) to a human being or an animal. The present invention also relates to pharmaceutical compositions comprising a compound of formula (I) and a pharmaceutically acceptable carrier and/or adjuvant. Furthermore, the present invention relates to the use of such compounds for the preparation of medicaments for the treatment of disorders which are associated with cysteine proteases. The present invention also relates to processes for the preparation of the compounds of formula (I).

DEFINITIONS

Unless otherwise indicated the following definitions are set forth to illustrate and define the meaning and scope of the various terms used to describe the invention herein.

In this specification the term "lower" is used to mean a group consisting of one to seven, preferably of one to four carbon atoms(s).

The term "alkyl" refers to a branched or straight chain monovalent saturated aliphatic hydrocarbon radical of one to eight carbon atoms.

The term "lower-alkyl" refers to a branched or straight chain monovalent alkyl radical of one to six carbon atoms, preferably one to four carbon atoms. This term is further exemplified by such radicals as methyl, ethyl, n-propyl, isopropyl, n-butyl, s-butyl, t-butyl and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Cycloalkyl" means a monovalent saturated carboncyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof such as cyclohexenyl, cyclopentenyl, and the like.

"Cycloalkylalkyl" means a moiety of the formula —R'—R", where R' is alkylene and R" is cycloalkyl as defined herein.

"Alkylamino" or "Monoalkylamino" means a radical —NHR where R represents an alkyl, cycloalkyl or cycloalkyl-alkyl group as defined herein. Representative examples include, but are not limited to methylamino, ethylamino, isopropylamino, cyclohexylamino, and the like.

"Dialkylamino" means a radical —NRR' where R and R' independently represent an alkyl, cycloalkyl, or cycloalkylalkyl group as defined herein. Representative examples include, but are not limited to dimethylamino, methylethylamino, di(1-methylethyl)amino, (cyclohexyl)(methyl)amino, (cyclohexyl)(ethyl)amino, (cyclohexyl)(propyl)amino, (cyclohexylmethyl)(methyl)amino, (cyclohexylmethyl)(ehtyl)amino, and the like.

The term "halo" refers to fluorine, chlorine, bromine and iodine, with fluorine, chlorine and bromine being preferred.

"Haloalkyl" means alkyl substituted with one or more same or different halo atoms, e.g., —$CH_2Cl$, —$CF_3$, —$CH_2CF_3$, —$CH_2CCl_3$, and the like.

"Heteroalkyl" means an alkyl radical as defined herein wherein one, two or three hydrogen atoms have been replaced with a substituent independently selected from the group consisting of —$ORa$, —$NRbRc$, and —$S(O)nRd$ (where n is an integer from 0 to 2), with the understanding that the point of attachment of the heteroalkyl radical is through a carbon atom, wherein Ra is hydrogen, acyl, alkyl, cycloalkyl, or cycloalkylalkyl; Rb and Rc are independently of each other hydrogen, acyl, alkyl, cycloalkyl, or cycloalkylalkyl; when n is 0, Rd is hydrogen, alkyl, cycloalkyl, or cycloalkylalkyl, and when n is 1 or 2, Rd is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one or more substituents, preferably one or two substituents, selected from alkyl, haloalkyl, hydroxyalkyl, heteroalkyl, acyl, alkylene-C(O)—XR (where X is a bond, O or NR' (where R' is hydrogen or lower-alkyl) and R is hydrogen, alkyl, alkenyl, hydroxy, alkoxy, amino, monoalkylamino or dialkylamino) acylamino, amino, monoalkylamino, dialkylamino, NR'C(O)OR" (where R' is hydrogen or alkyl and R" is alkyl or alkenyl), alkylthio, alkylsulfinyl, alkylsulfonyl, —$SO_2NR'R"$ (where R' and R"

are independently hydrogen, alkyl, cycloalkyl or cycloalkyl-alkyl), NRSO$_2$R' (where R is hydrogen or lower alkyl, and R' is alkyl, cycloalkyl, cycloalkyl-alkyl, amino, monoalkylamino or dialkylamino), alkoxy, haloalkxy, alkoxycarbonyl, carbamoyl, hydroxy, halo, nitro, cyano, cyanoalkyl, mercapto, methylenedioxy, ethylenedioxy, benzyloxy, heterocyclyl-alkoxy or optionally substituted phenyl. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl, thazinanyl and the like, including partially hydrogenated derivates thereof.

"Heteroarylalkyl" and "heteroaralkyl", which may be used interchangeably, mean a radical —R$^a$R$^b$ where R$^a$ is an alkylene group and R$^b$ is a heteroaryl group as defined herein; e.g., thienylmethyl, pyridinylmethyl, imidazolylethyl, pyrazolylpropyl, and the like are examples of heteroarylalkyl.

"Heterocyclyl" means a saturated or unsaturated non-aromatic cyclic radical of 3 to 8 ring atoms in which one or two ring atoms are heteroatoms selected from N, N(O), O, or S(O)$_n$ (where n is an integer from 0 to 2), the remaining ring atoms being C. The heterocyclyl ring may be optionally substituted independently with one, two, or three substituents selected from alkyl, haloalkyl, heteroalkyl, halo, nitro, cyanoalkyl, hydroxy, alkoxy, amino, monoalkylamino or dialkylamino. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxaxolidinyl, isoxazolidinyl, morpholinyl, thiazolidinyl, isothiazolidinyl, quinuclidinyl, qunioliinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like, including partially unsaturated derivatives thereof.

"Heterocyclylalkyl" means a group —R$^x$—R$^y$ where R$^x$ is an alkylene group and R$^y$ is a heterocyclyl group. Representative examples include, but are not limited to, 2-(morpholin-4-yl)ethyl, 2-(4-methyl-piperazin-1-yl)ethyl, 3-(piperidin-1-yl)propyl and the like.

"Heterocyclyl-alkoxy" means a group —OR$^x$—R$^y$ where R$^x$ is an alkylene group and R$^y$ is a heterocyclyl group. Representative examples include, but are not limited to 2-(morpholin-4-yl)ethoxy, 2-(4-methyl-piperazin-1-yl) ethoxy and the like.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl, preferably 2-hydroxyethyl, 2,3-dihydroxypropyl and 1-(hydroxymethyl)-2-hydroxyethyl. Accordingly, as used herein, the term "hydroxyalkyl" is used to define a subset of heteroalkyl groups.

The term "alkoxy" refers to the group R'—O—, wherein R' is an alkyl. The term "lower-alkoxy" refers to the group R'—O—, wherein R' is a lower-alkyl.

The term "alkenyl" stands for alone or in combination with other groups, a straight-chain or branched hydrocarbon residue containing an olefinic bond and up to 20, preferably up to 16 C-atoms. The term "lower-alkenyl" refers to a straight-chain or branched hydrocarbon residue containing an olefinic bond and up to 7, preferably up to 4 C-atoms.

"Aryl" means a monocyclic or bicyclic aromatic hydrocarbon radical which is optionally substituted with one or more substituents, preferably one, two or three, substituents preferably selected from the group consisting of alkyl, haloalkyl, hydroxyalkyl, heteroalkyl, acyl, acylamino, amino, alkylamino, dialkylamino, alkylthio, alkylsulfinyl, alkylsulfonyl, —SO$_2$NR'R" (where R' and R" are independently hydrogen or alkyl), alkoxy, haloalkoxy, alkoxycarbonyl, carbamoyl, hydroxy, halo, nitro, cyano, mercapto, methylenedioxy or ethylenedioxy. More specifically the term aryl includes, but is not limited to, phenyl, chlorophenyl, fluorophenyl, methoxyphenyl, 1-naphthyl, 2-naphthyl, and the derivatives thereof.

"Arylalkyl" and "Aralkyl", which may be used interchangeably, mean a radical —R$^a$R$^b$ where R$^a$ is an alkylene group and R$^b$ is an aryl group as defined herein; e.g., benzyl, phenylethyl, 3-(3-chlorophenyl)-2-methylpentyl, and the like are examples of arylalkyl.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

The term "pharmaceutically acceptable esters" embraces esters of the compounds of formula (1), in which hydroxy groups have been converted to the corresponding esters with inorganic and organic acids such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

All references, patents and publications cited in this disclosure are incorporated herein by reference in their entirety.

Nomenclature and Chemical Structures

In general, the nomenclature used in the Application is based on AutoNom®, a Beilstein Institute computerized system for the generation of IUPAC systemic monmenclature. Chemical structures shown herein were prepared using ISIS®version 2.2. Any open valency shown on a carbon, nitrogen or oxygen in the structures herein indicates the presence of a hydrogen. Nitrile or cyano groups are shown herein as —CN and —≡N, which may be used interchangeably.

Compounds

The compounds of the invention have an inhibitory activity on cysteine proteases, more particularly on cysteine proteases of the papain superfamily, even more particularly on cysteine proteases of the cathepsin family, most particularly on cathepsin K. It was surprisingly found, that this inhibiting effect on cathepsin K is selective with respect to other cathepsins. While compounds of general formula (I)

very efficiently inhibit cathepsin K, the inhibition of other protease inhibitors such as cathepsin S, cathepsin L and cathepsin B is much weaker. Therefore the new compounds of general formula (I) are useful for specifically inhibiting cathepsin K. They can accordingly be used for the treatment of disorders which are associated with cysteine proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease.

The subject compounds are of the formula (I)

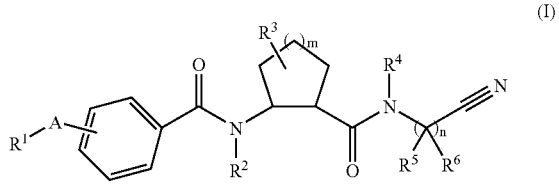

(I)

wherein:

m is from 1 to 3;

n is 1 or 2;

A is: $-(CR^aR^b[[_2]])_p-$; $-O-(CR^aR^b[[_2]])_s-$, $-NR^c-(CR^aR^b[[_2]])_t-$; or $-CH=CH-$;

wherein p and s each individually is from 0 to 3, t is from 1 to 3, and $R^a$, $R^b$ and $R^c$ each independently is hydrogen or alkyl;

$R^1$ is: halo; alkyl; alkenyl; alkoxy; hydroxy; amino; aryl; heteroaryl; heterocyclyl; $-S(O)_q-R^d$; $-NR^dS(O)_q-R^e$; or $-S(O)_q-NR^dR^e$ wherein q is from 0 to 2, $R^d$ is hydrogen, alkyl or optionally substituted phenyl and $R^e$ is hydrogen, alkyl, or pyridinylmethyl;

$R^2$, $R^3$, $R^4$ and $R^5$ each independently is hydrogen or alkyl; and $R^6$ is hydrogen, alkyl, optionally substituted benzyl, thienylmethyl, pyridylmethyl, cycloalkyl, or $-(CR^fR^g)_TS(O)_q-R^h$ where $R^f$, $R^g$ and $R^h$ each independently is hydrogen or alkyl and n is from 0 to 2;

with the proviso that when $R^1$ is halo or optionally substituted phenyl, $R^6$ is optionally substituted benzyl, thienylmethyl, pyridylmethyl, or $-(CR^fR^g)_TS(O)_q-R^h$; and pharmaceutically acceptable salts, solvents or prodrugs thereof.

Where any of $R^1$, $R^2$, $R^3$, $R^4$, $R^5$, $R^6$, $R^a$, $R^b$, $R^c$, $R^d$, $R^e$, $R^f$, $R^g$ or $R^h$ are alkyl, they are in many embodiments lower alkyl, i.e. $C_1$-$C_6$alkyl, and more specifically $C_1$-$C_4$alkyl.

In embodiments wherein $R^1$ aryl, it is preferably optionally substituted phenyl.

Where $R^1$ is heteroaryl, $R^1$ may be an optionally substituted heteroaryl selected from pyrolyl, thiazolyl, oxazolyl, thienyl, imidazolyl, triazolyl, furyl, pyridinyl, and pyrazolyl. In certain embodiments $R^1$ may be selected from pyrrol-1-yl, 1,3-thiazol-4-yl, 1,3-thiazol-2-yl, 2-methyl-1,3-thiazol-4-yl, 2-(piperidin-4-yl-amino)-1,3-thiazol-4-yl, 2-[aminopiperidin-(1-carboxylate allyl ester)-4-yl]-1,3-thiazol-2-yl, 4-chloromethyl-1,3-thiazol-2-yl, 1,3-oxazol-5-yl, oxazol-4-yl, thien-2-yl, 5-bromothien-2-yl, 5-methylthien-2-yl, imidazol-1-yl, imidazol-5-yl, 1-methylimidazol-5-yl, 1-methylimidazol-2-yl, 1,2,4-triazolyl, 2-furyl, pyridin-3-yl, pyridin-2-yl, pyridin-4-yl, 6-methylpyridin-3-yl, 5-methylpyridin-3-yl, 6-methylpyridin-2-yl, pyrazol-5-yl, pyrazol-1-yl and methylpyrazol-3-yl.

In embodiments where $R^1$ is heterocyclyl, $R^1$ may be optionally substituted heterocyclyl selected from morpholinyl, piperazinyl, piperdinyl, pyrrolidinyl, thiomorpholinyl, thiazinanyl, oxidothiomorpholinyl, dioxidothiomorpholinyl, oxidothiazinanyl, dioxidothiazinanyl, and 1,1,3-trioxidothiomorpholinyl. In certain embodiments, $R^1$ may be selected from piperidin-4-yl, piperidin-(1-carboxylate allyl ester)-4-yl, morpholin-4-yl, piperazin-1-yl, 4-methylpiperazin-1-yl, 4-n-propylpiperazin-1-yl, 4-isopropylpiperazin-1-yl, 4-benzylpiperazin-1-yl, piperidin-1-yl, 1-n-propylpiperidin-4-yl, 1-ethylpiperidin-4-yl, 1-(2-methoxyethyl)piperidin-4-yl, 4-(1,1,4-trioxidothiomorpholin-4-yl), 4-(1,1-dioxido-1,2-thiazinan-2-yl, pyrrolidin-1-yl and 4-(1,1-dioxidothiomorpholin-4-yl).

In embodiments of the invention where $R^6$ alkyl, $R^6$ may be isobutyl. Where $R^6$ is cycloalkyl, $R^6$ may in certain embodiments be cyclopropyl. Where $R^6$ is aryl, $R^6$ may be optionally substituted benzyl, such as 3,4-difluorobenzyl or 4-nitrobenzyl. In embodiments where $R^6$ is heteroarylalkyl, $R^6$ may be thienylmethyl such as thien-3-yl-methyl, or pyridylmethyl such as pyridin-2-ylmethyl, pyridin-3-ylmethyl and pyridin-4-ylmethyl, which may be optionally substituted.

In many embodiments m is 2, n is 1, $R^2$, $R^3$, $R^4$, $R^5$, $R^a$, $R^b$, $R^c$, $R^f$ and $R_g$ are hydrogen, and the group $R^1$—A—is in the 4-position with respect to the adjacent benzamide functionality. In such embodiments the compounds of the invention may be represented by the formula (II):

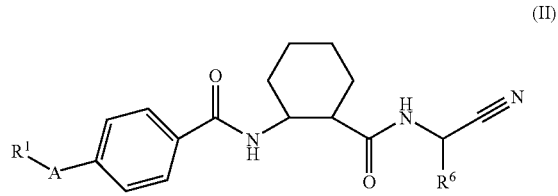

(II)

wherein A, $R^1$ and $R^6$ are as defined herein. In certain embodiments the stereochemistry of the subject compounds may be such that the compounds are of the formula (III):

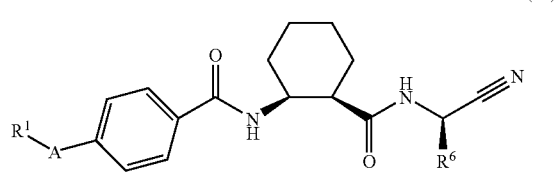

(III)

wherein A, $R^1$ and $R^6$ again are as defined herein.

Representative compounds in accordance with the invention are shown in Table 1. The Experimental Examples (Methods) associated with preparation of the individual compounds are referenced in Table 1.

TABLE 1

| # | Structure | Method | Name |
|---|---|---|---|
| 1. | 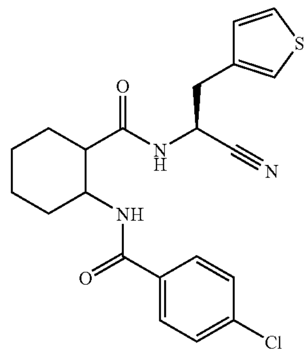 | E | 4-chloro-N-[2-({[(1S)-1-cyano-2-thien-3-ylethyl]amino}carbonyl)cyclohexyl]benzamide |
| 2. | 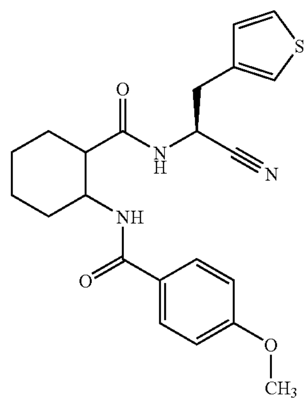 | E | N-[2-({[(1S)-1-cyano-2-thien-3-ylethyl]amino}carbonyl)cyclohexyl]-4-methoxybenzamide |
| 3. | 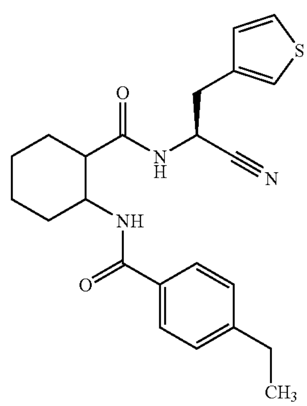 | E | N-[2-({[(1S)-1-cyano-2-thien-3-ylethyl]amino}carbonyl)cyclohexyl]-4-ethylbenzamide |
| 4. | 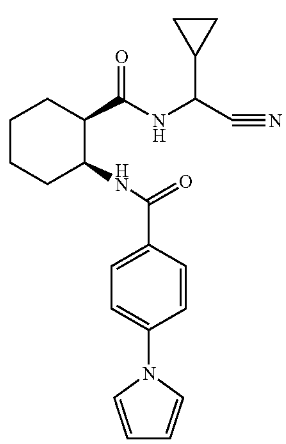 | A | N-[(1S,2R)-2-({[cyano(cyclopropyl)methyl]amino}carbonyl)cyclohexyl]-4-(1H-pyrrol-1-yl)benzamide |

TABLE 1-continued

| # | Structure | Method | Name |
|---|---|---|---|
| 5. | 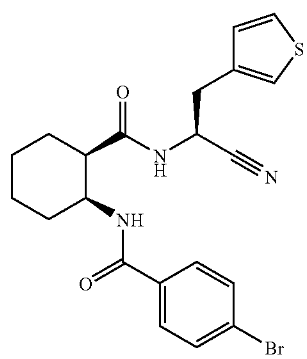 | E | 4-bromo-N-[(1S,2R)-2-({[(1S)-1-cyano-2-thien-3-ylethyl]amino}carbonyl)cyclohexyl]benzamide |
| 6. | 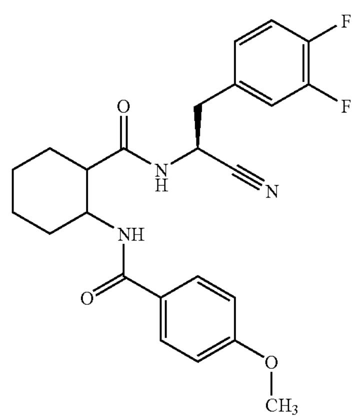 | E | N-[2-({[(1S)-1-cyano-2-(3,4-difluorophenyl)ethyl]amino}carbonyl)cyclohexyl]-4-methoxybenzamide |
| 7. | 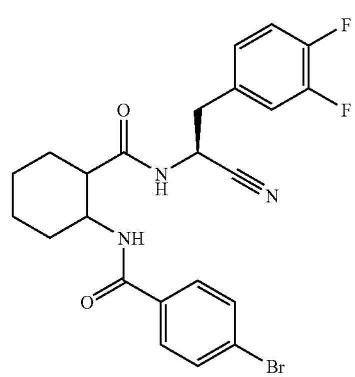 | E | 4-bromo-N-[2-({[(1S)-1-cyano-2-(3,4-difluorophenyl)ethyl]amino}carbonyl)cyclohexyl]benzamide |
| 8. | 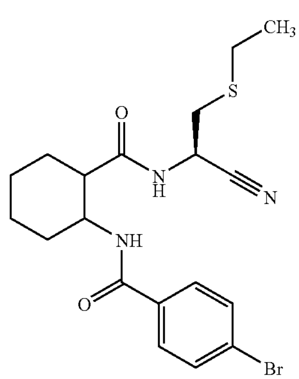 | E | 4-bromo-N-[2-({[(1R)-1-cyano-2-(ethylthio)ethyl]amino}carbonyl)cyclohexyl]benzamide |

TABLE 1-continued

| # | Structure | Method | Name |
|---|-----------|--------|------|
| 9. | 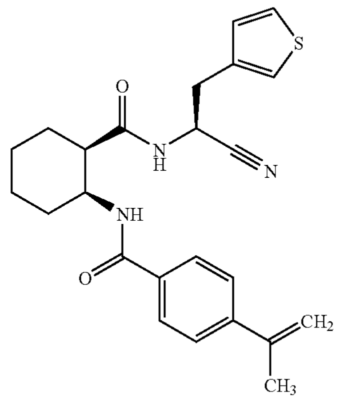 | E | N-[(1S,2R)-2-({[(1S)-1-cyano-2-thien-3-ylethyl]amino}carbonyl)cyclohexyl]-4-isopropenylbenzamide |
| 10. | 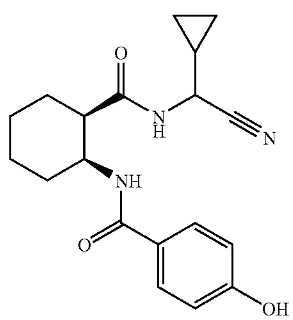 | A | N-[(1S,2R)-2-({[cyano(cyclopropyl)methyl]amino}carbonyl)cyclohexyl]-4-hydroxybenzamide |
| 11. | 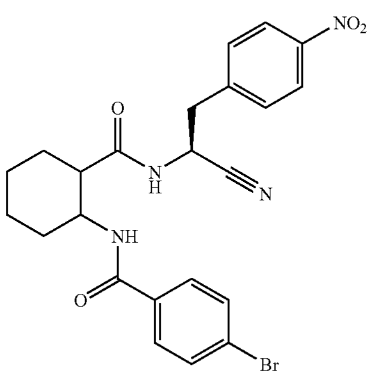 | E | 4-bromo-N-[2-({[(1S)-1-cyano-2-(4-nitrophenyl)ethyl]amino}carbonyl)cyclohexyl]benzamide |

TABLE 1-continued

| # | Structure | Method | Name |
|---|---|---|---|
| 12. | 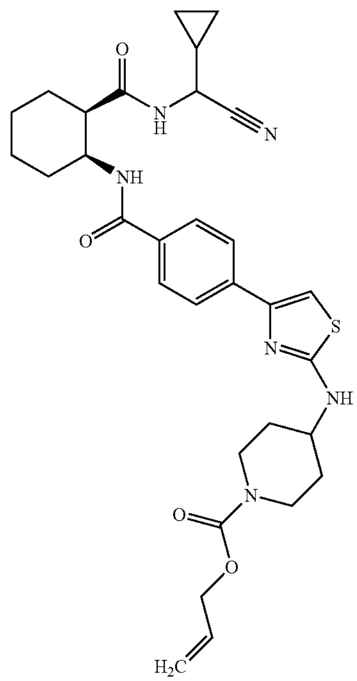 | C | Allyl 4-({4-[4-({[(1S,2R)-2-({[cyano(cyclopropyl)methyl]amino}carbonyl)cyclohexyl]amino}carbonyl)phenyl]-1,3-thiazol-2-yl}amino)piperidine-1-carboxylate |
| 13. | 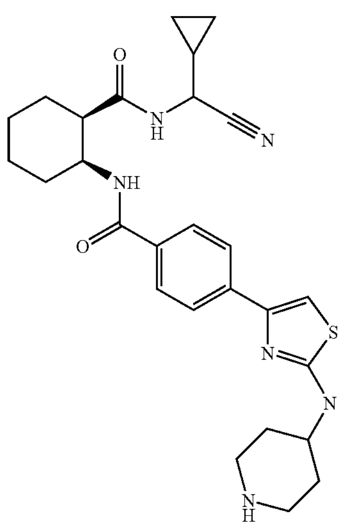 | C | N-[(1S,2R)-2-({[cyano(cyclopropyl)methyl]amino}carbonyl)cyclohexyl]-4-[2-(piperidin-4-ylamino)-1,3-thiazol-4-yl]benzamide trifluoroacetate |
| 14. | 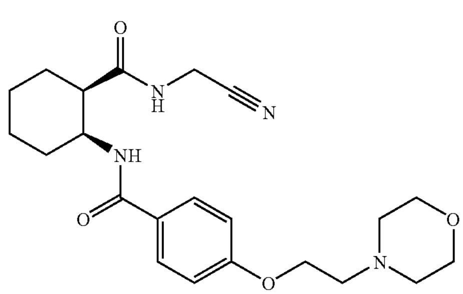 | A | N-((1S,2R)-2-{[(cyanomethyl)amino]carbonyl}cyclohexyl)-4-(2-morpholin-4-ylethoxy)benzamide |

TABLE 1-continued

| # | Structure | Method | Name |
|---|---|---|---|
| 15. | 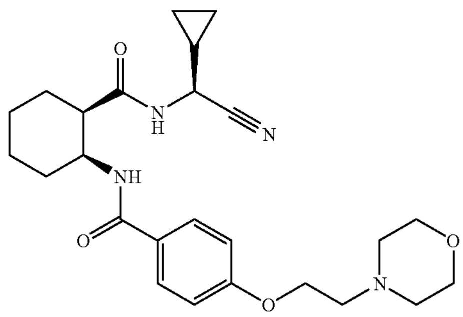 | A | N-[(1S,2R)-2-({[(S)-cyano(cyclopropyl)methyl]amino}carbonyl)cyclohexyl]-4-(2-morpholin-4-ylethoxy)benzamide |
| 16. | 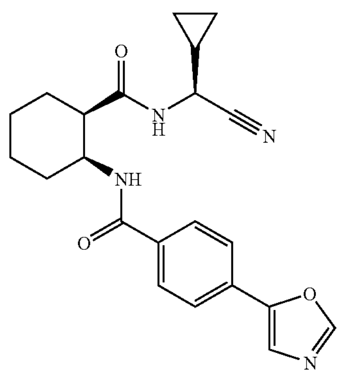 | B | N-[(1S,2R)-2-({[(S)-cyano(cyclopropyl)methyl]amino}carbonyl)cyclohexyl]-4-(1,3-oxazol-5-yl)benzamide |
| 17. | 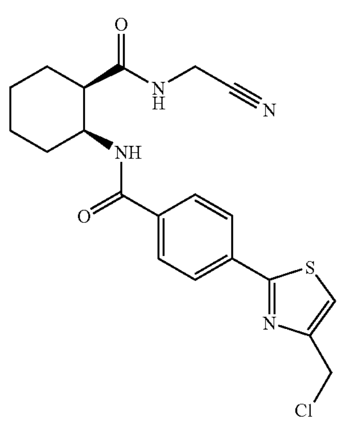 | E | 4-[4-(chloromethyl)-1,3-thiazol-2-yl]-N-((1S,2R)-2-{[(cyanomethyl)amino]carbonyl}cyclohexyl)benzamide |
| 18. | 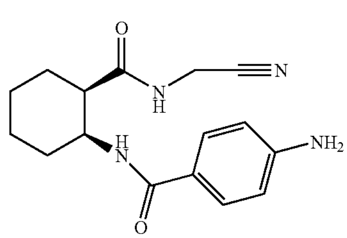 | A | 4-amino-N-((1S,2R)-2-{[(cyanomethyl)amino]carbonyl}cyclohexyl)benzamide |

TABLE 1-continued

| # | Structure | Method | Name |
|---|-----------|--------|------|
| 19. | 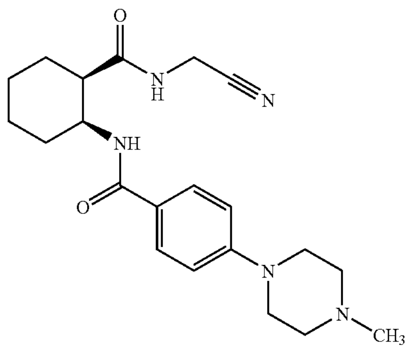 | A | N-((1S,2R)-2-{[(cyanomethyl)amino]carbonyl}cyclohexyl)-4-(4-methylpiperazin-1-yl)benzamide |
| 20. | 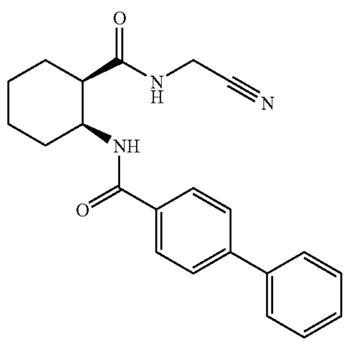 | A | N-((1S,2R)-2-{[(cyanomethyl)amino]carbonyl}cyclohexyl)-1,1'-biphenyl-4-carboxamide |
| 21. | 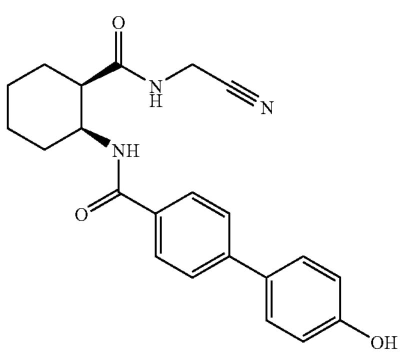 | A | N-((1S,2R)-2-{[(cyanomethyl)amino]carbonyl}cyclohexyl)-4'-hydroxy-1,1'-biphenyl-4-carboxamide |
| 22. | 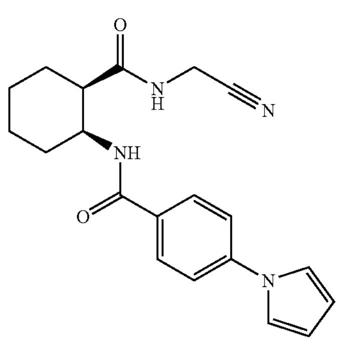 | A | N-((1S,2R)-2-{[(cyanomethyl)amino]carbonyl}cyclohexyl)-4-(1H-pyrrol-1-yl)benzamide |

TABLE 1-continued

| # | Structure | Method | Name |
|---|---|---|---|
| 23. | 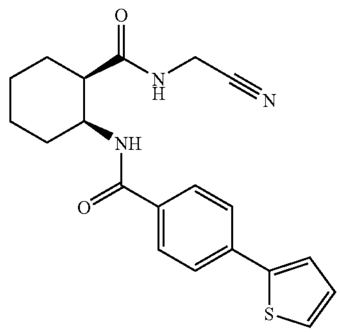 | A | N-((1S,2R)-2-{[(cyanomethyl)amino]carbonyl}cyclohexyl)-4-thien-2-ylbenzamide |
| 24. | 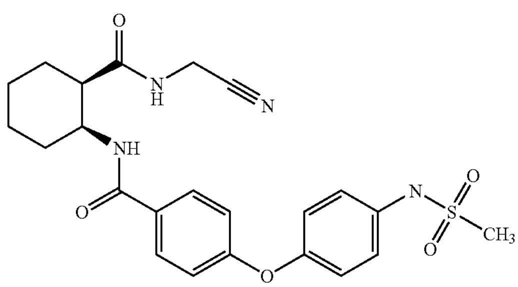 | A | N-((1S,2R)-2-{[(cyanomethyl)amino]carbonyl}cyclohexyl)-4-{4-[(methylsulfonyl)amino]phenoxy}benzamide |
| 25. | 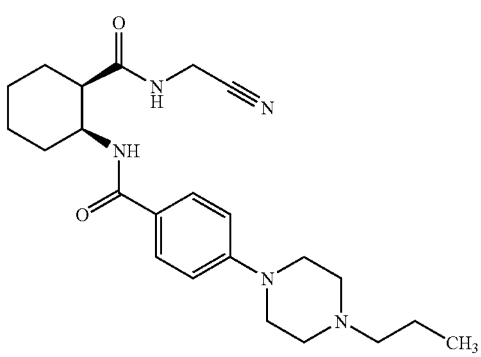 | A | N-((1S,2R)-2-{[(cyanomethyl)amino]carbonyl}cyclohexyl)-4-(4-propylpiperazin-1-yl)benzamide |
| 26. | 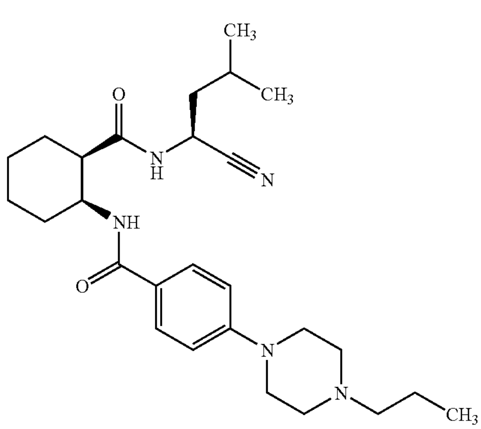 | B | N-[(1S,2R)-2-({[(1S)-1-cyano-3-methylbutyl]amino}carbonyl)cyclohexyl]-4-(4-propylpiperazin-1-yl)benzamide |

TABLE 1-continued

| # | Structure | Method | Name |
|---|---|---|---|
| 27. | 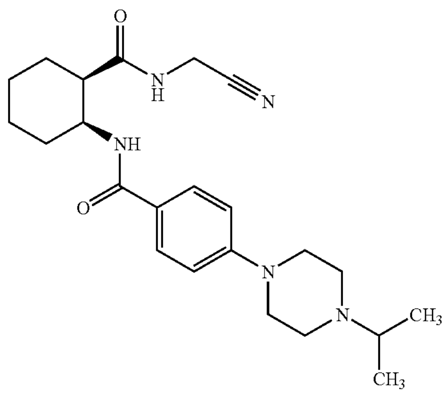 | A | N-((1S,2R)-2-{[(cyanomethyl)amino]carbonyl}cyclohexyl)-4-(4-isopropylpiperazin-1-yl)benzamide |
| 28. | 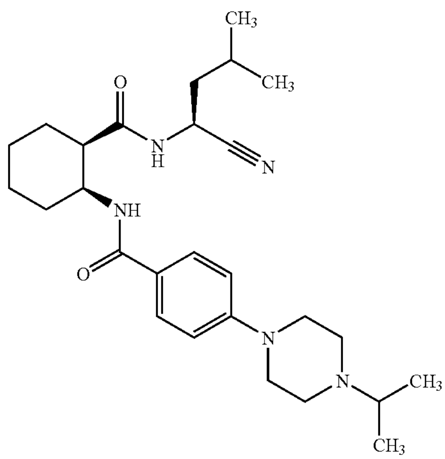 | B | N-[(1S,2R)-2-({[(1S)-1-cyano-3-methylbutyl]amino}carbonyl)cyclohexyl]-4-(4-isopropylpiperazin-1-yl)benzamide |
| 29. | 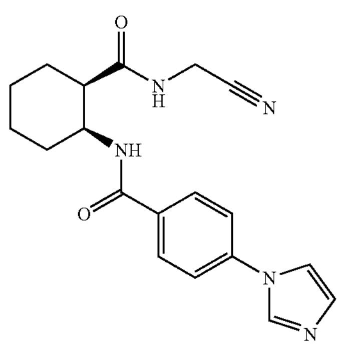 | A | N-((1S,2R)-2-{[(cyanomethyl)amino]carbonyl}cyclohexyl)-4-(1H-imidazol-1-yl)benzamide |
| 30. | 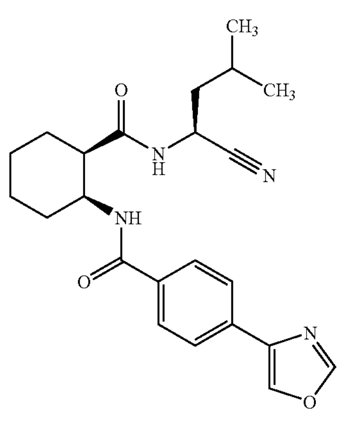 | D | N-[(1S,2R)-2-({[(1S)-1-cyano-3-methylbutyl]amino}carbonyl)cyclohexyl]-4-(1,3-oxazol-4-yl)benzamide |

TABLE 1-continued

| # | Structure | Method | Name |
|---|---|---|---|
| 31. | 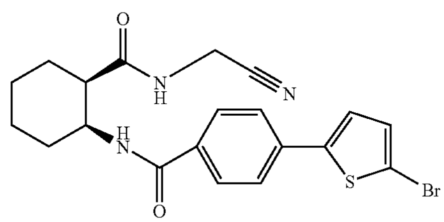 | A | 4-(5-bromothien-2-yl)-N-((1S,2R)-2-{[(cyanomethyl)amino]carbonyl}cyclohexyl)benzamide |
| 32. | 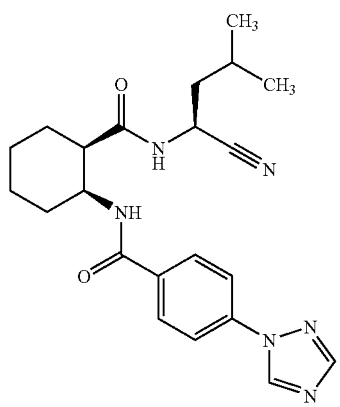 | D | N-[(1S,2R)-2-({[(1S)-1-cyano-3-methylbutyl]amino}carbonyl)cyclohexyl]-4-(1H-1,2,4-triazol-1-yl)benzamide |
| 33. | 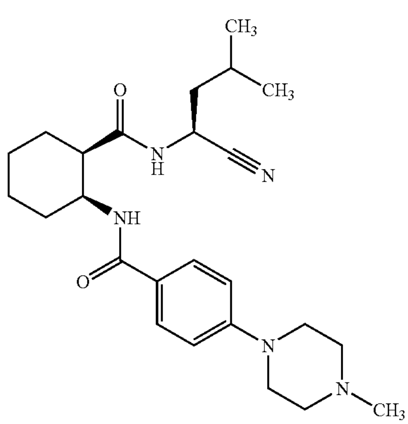 | B | N-[(1S,2R)-2-({[(1S)-1-cyano-3-methylbutyl]amino}carbonyl)cyclohexyl]-4-(4-methylpiperazin-1-yl)benzamide |
| 34. | 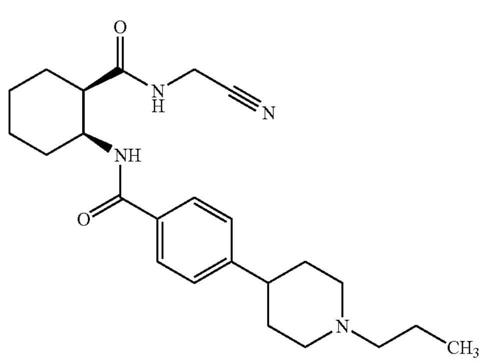 | C | N-((1S,2R)-2-{[(cyanomethyl)amino]carbonyl}cyclohexyl)-4-(1-propylpiperidin-4-yl)benzamide |

TABLE 1-continued

| # | Structure | Method | Name |
|---|---|---|---|
| 35. | 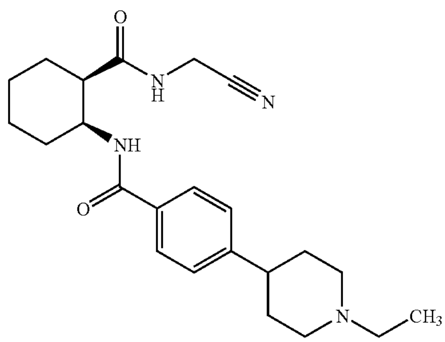 | C | N-((1S,2R)-2-{[(cyanomethyl)amino]carbonyl}cyclohexyl)-4-(1-ethylpiperidin-4-yl)benzamide |
| 36. | 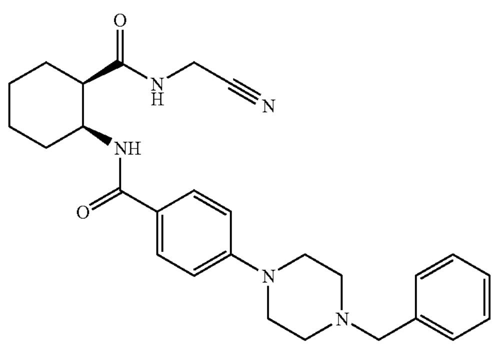 | A | 4-(4-benzylpiperazin-1-yl)-N-((1S,2R)-2-{[(cyanomethyl)amino]carbonyl}cyclohexyl)benzamide |
| 37. | 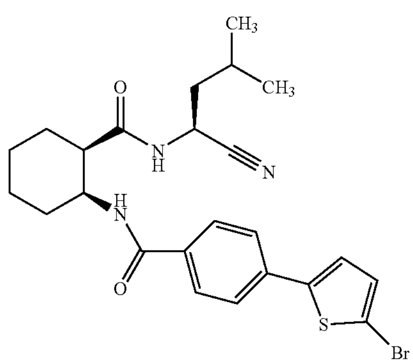 | B | 4-(5-bromothien-2-yl)-N-[(1S,2R)-2-({[(1S)-1-cyano-3-methylbutyl]amino}carbonyl)cyclohexyl]benzamide |
| 38. | 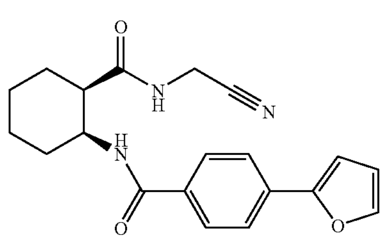 | A | N-((1S,2R)-2-{[(cyanomethyl)amino]carbonyl}cyclohexyl)-4-(2-furyl)benzamide |

TABLE 1-continued

| # | Structure | Method | Name |
|---|---|---|---|
| 39. | 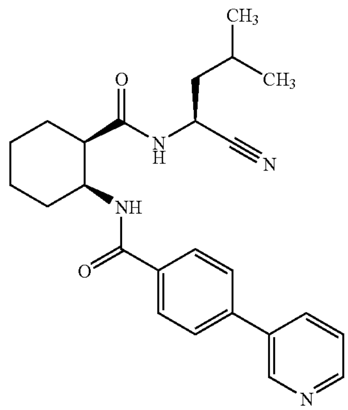 | D | N-[(1S,2R)-2-({[(1S)-1-cyano-3-methylbutyl]amino}carbonyl)cyclohexyl]-4-pyridin-3-ylbenzamide |
| 40. | 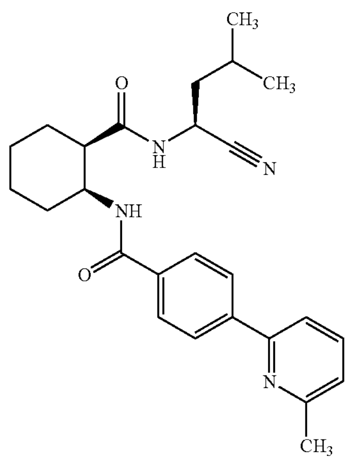 | D | N-[(1S,2R)-2-({[(1S)-1-cyano-3-methylbutyl]amino}carbonyl)cyclohexyl]-4-(6-methylpyridin-2-yl)benzamide |
| 41. | 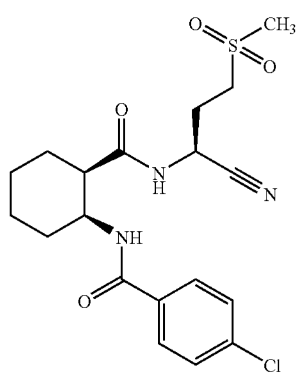 | B | 4-chloro-N-[(1S,2R)-2-({[(1S)-1-cyano-3-(methylsulfonyl)propyl]amino}carbonyl)cyclohexyl]benzamide |
| 42. | 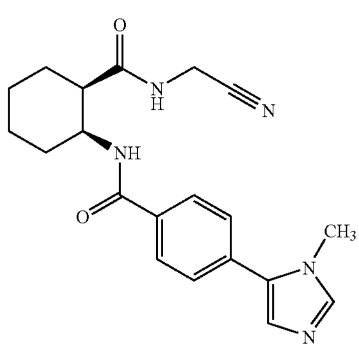 | C | N-((1S,2R)-2-{[(cyanomethyl)amino]carbonyl}cyclohexyl)-4-(1-methyl-1H-imidazol-5-yl)benzamide |

TABLE 1-continued

| # | Structure | Method | Name |
|---|---|---|---|
| 43. | 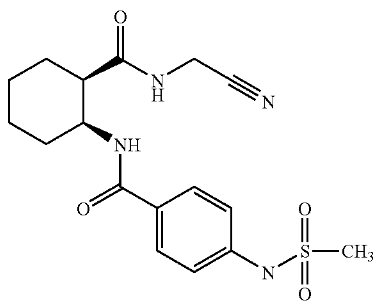 | A | N-((1S,2R)-2-{[(cyanomethyl)amino]carbonyl}cyclohexyl)-4-[(methylsulfonyl)amino]benzamide |
| 44. | 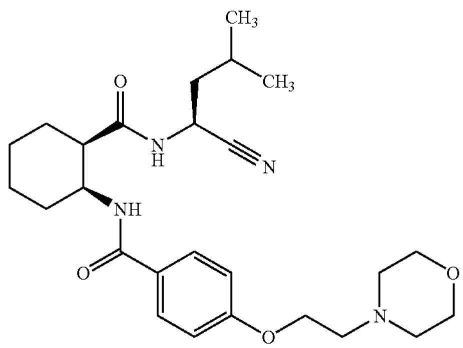 | E | N-[(1S,2R)-2-({[(1S)-1-cyano-3-methylbutyl]amino}carbonyl)cyclohexyl]-4-(2-morpholin-4-ylethoxy)benzamide |
| 45. | 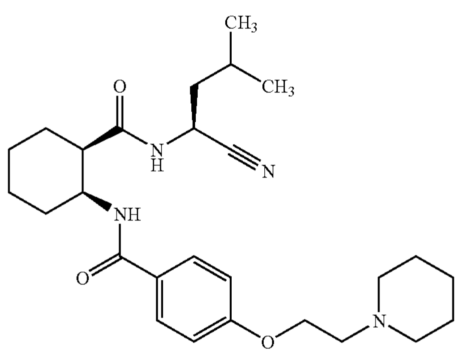 | B | N-[(1S,2R)-2-({[(1S)-1-cyano-3-methylbutyl]amino}carbonyl)cyclohexyl]-4-(2-piperidin-1-ylethoxy)benzamide |
| 46. | 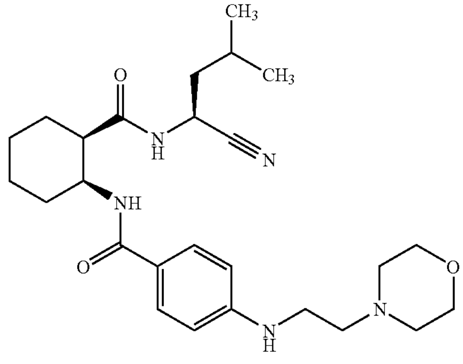 | D | N-[(1S,2R)-2-({[(1S)-1-cyano-3-methylbutyl]amino}carbonyl)cyclohexyl]-4-[(2-morpholin-4-ylethyl)amino]benzamide |

TABLE 1-continued

| # | Structure | Method | Name |
|---|-----------|--------|------|
| 47. | 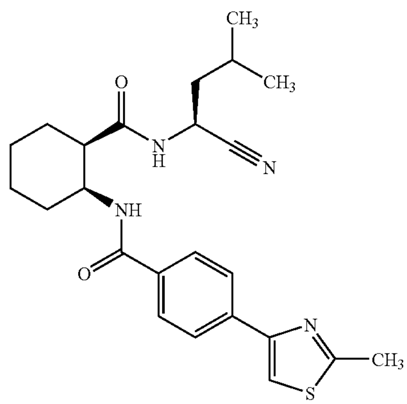 | D | N-[(1S,2R)-2-({[(1S)-1-cyano-3-methylbutyl]amino}carbonyl)cyclohexyl]-4-(2-methyl-1,3-thiazol-4-yl)benzamide |
| 48. | 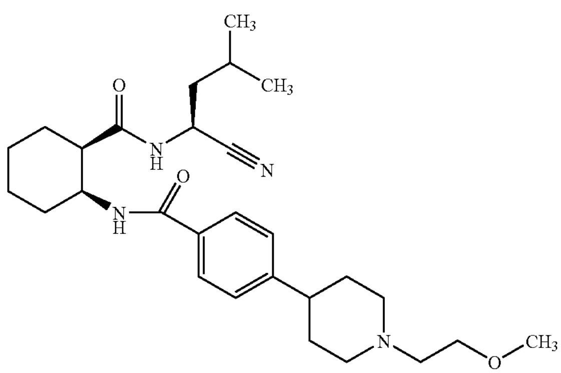 | D | N-[(1S,2R)-2-({[(1S)-1-cyano-3-methylbutyl]amino}carbonyl)cyclohexyl]-4-[1-(2-methoxyethyl)piperidin-4-yl]benzamide |
| 49. | 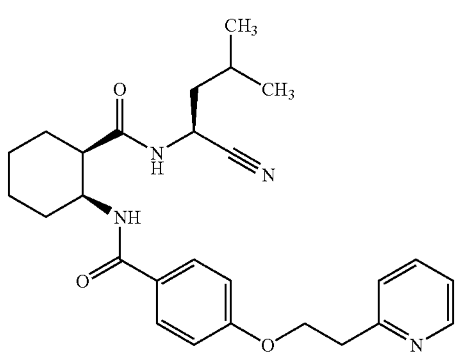 | D | N-[(1S,2R)-2-({[(1S)-1-cyano-3-methylbutyl]amino}carbonyl)cyclohexyl]-4-(2-pyridin-2-ylethoxy)benzamide |
| 50. | 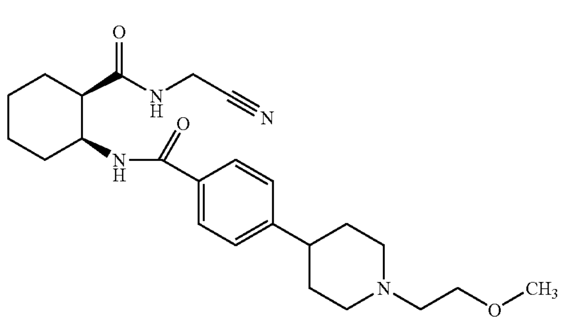 | C | N-((1S,2R)-2-{[(cyanomethyl)amino]carbonyl}cyclohexyl)-4-[1-(2-methoxyethyl)piperidin-4-yl]benzamide |

TABLE 1-continued

| # | Structure | Method | Name |
|---|-----------|--------|------|
| 51. | 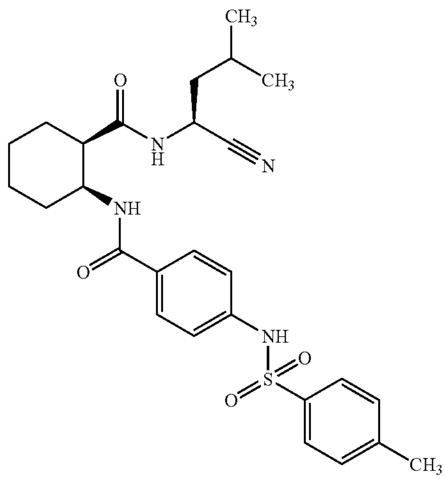 | D | N-[(1S,2R)-2-({[(1S)-1-cyano-3-methylbutyl]amino}carbonyl)cyclohexyl]-4-{[(4-methylphenyl)sulfonyl]amino}benzamide |
| 52. | 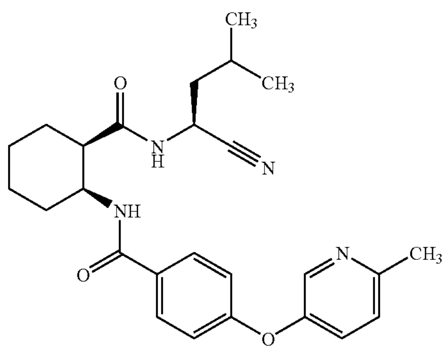 | D | N-[(1S,2R)-2-({[(1S)-1-cyano-3-methylbutyl]amino}carbonyl)cyclohexyl]-4-[(6-methylpyridin-3-yl)oxy]benzamide |
| 53. | 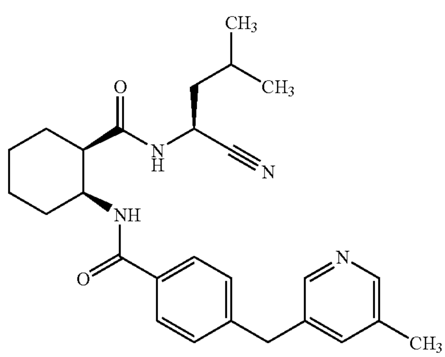 | D | N-[(1S,2R)-2-({[(1S)-1-cyano-3-methylbutyl]amino}carbonyl)cyclohexyl]-4-[(5-methylpyridin-3-yl)methyl]benzamide |
| 54. | 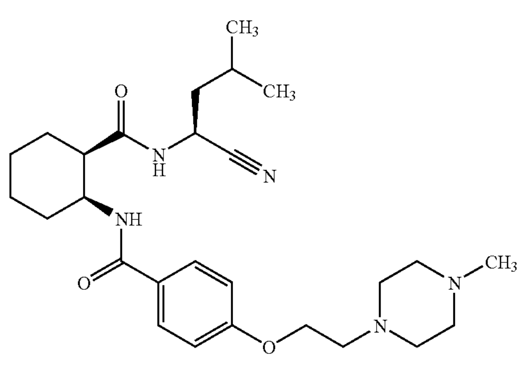 | D | N-[(1S,2R)-2-({[(1S)-1-cyano-3-methylbutyl]amino}carbonyl)cyclohexyl]-4-[2-(4-methylpiperazin-1-yl)ethoxy]benzamide |

TABLE 1-continued

| # | Structure | Method | Name |
|---|---|---|---|
| 55. | 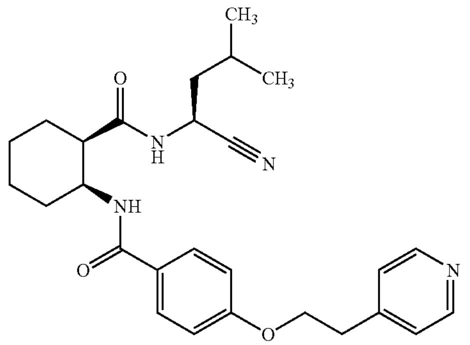 | D | N-[(1S,2R)-2-({[(1S)-1-cyano-3-methylbutyl]amino}carbonyl)cyclohexyl]-4-(2-pyridin-4-ylethoxy)benzamide |
| 56. | 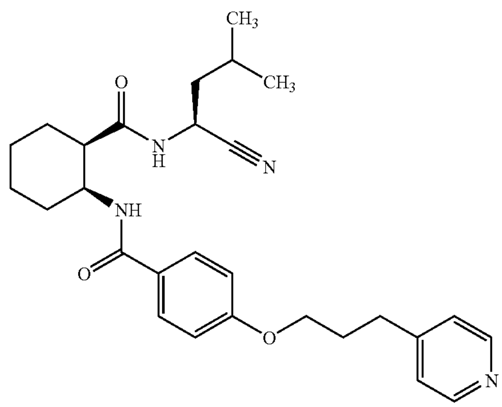 | D | N-[(1S,2R)-2-({[(1S)-1-cyano-3-methylbutyl]amino}carbonyl)cyclohexyl]-4-(3-pyridin-4-ylpropoxy)benzamide |
| 57. | 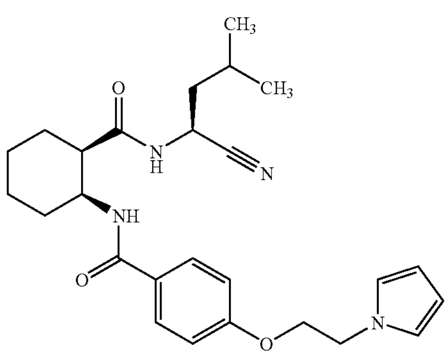 | D | N-[(1S,2R)-2-({[(1S)-1-cyano-3-methylbutyl]amino}carbonyl)cyclohexyl]-4-[2-(1H-pyrrol-1-yl)ethoxy]benzamide |
| 58. | 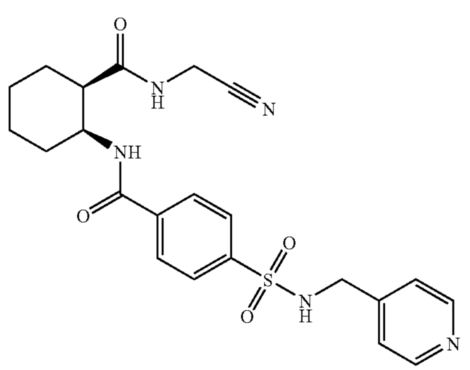 | C | N-((1S,2R)-2-{[(cyanomethyl)amino]carbonyl}cyclohexyl)-4-{[(pyridin-4-ylmethyl)amino]sulfonyl}benzamide |

TABLE 1-continued

| # | Structure | Method | Name |
|---|---|---|---|
| 59. | 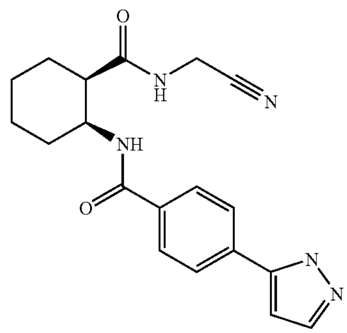 | C | N-((1S,2R)-2-{[(cyanomethyl)amino]carbonyl}cyclohexyl)-4-(1H-pyrazol-5-yl)benzamide |
| 60. | 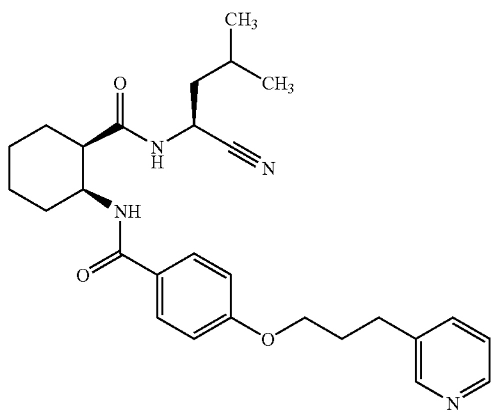 | D | N-[(1S,2R)-2-({[(1S)-1-cyano-3-methylbutyl]amino}carbonyl)cyclohexyl]-4-(3-pyridin-3-ylpropoxy)benzamide |
| 61. | 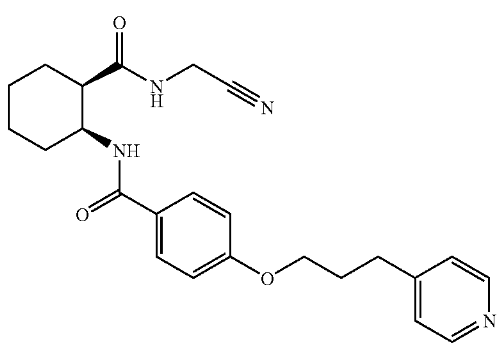 | A | N-((1S,2R)-2-{[(cyanomethyl)amino]carbonyl}cyclohexyl)-4-(3-pyridin-4-ylpropoxy)benzamide |
| 62. | 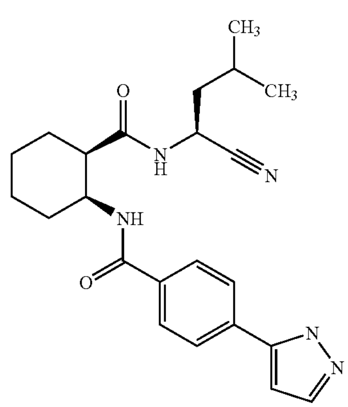 | D | N-[(1S,2R)-2-({[(1S)-1-cyano-3-methylbutyl]amino}carbonyl)cyclohexyl]-4-(1H-pyrazol-5-yl)benzamide |

TABLE 1-continued

| # | Structure | Method | Name |
|---|---|---|---|
| 63. | 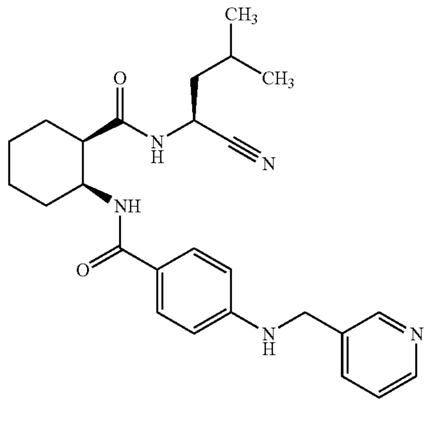 | D | N-[(1S,2R)-2-({[(1S)-1-cyano-3-methylbutyl]amino}carbonyl)cyclohexyl]-4-[(pyridin-3-ylmethyl)amino]benzamide |
| 64. | 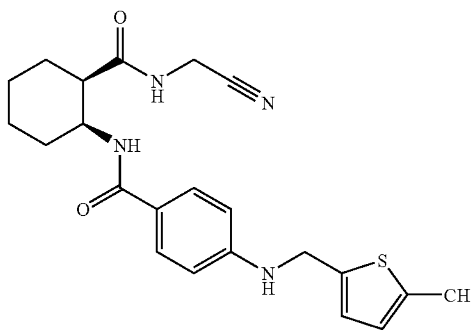 | C | N-((1S,2R)-2-{[(cyanomethyl)amino]carbonyl}cyclohexyl)-4-{[(5-methylthien-2-yl)methyl]amino}benzamide |
| 65. | 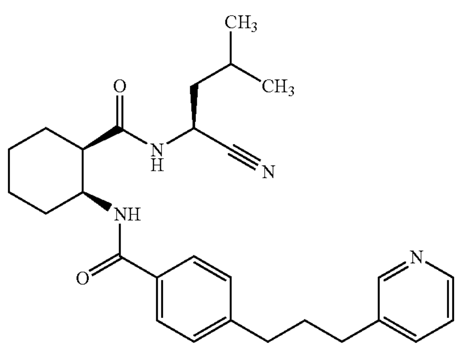 | D | N-[(1S,2R)-2-({[(1S)-1-cyano-3-methylbutyl]amino}carbonyl)cyclohexyl]-4-(3-pyridin-3-ylpropyl)benzamide |
| 66. | 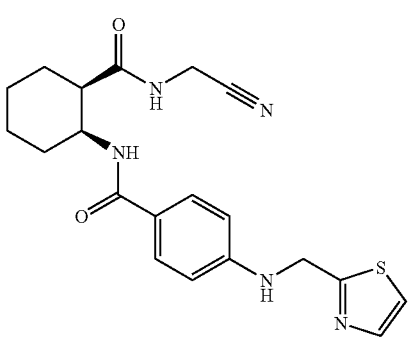 | C | N-((1S,2R)-2-{[(cyanomethyl)amino]carbonyl}cyclohexyl)-4-[(1,3-thiazol-2-ylmethyl)amino]benzamide |

TABLE 1-continued

| # | Structure | Method | Name |
|---|---|---|---|
| 67. | 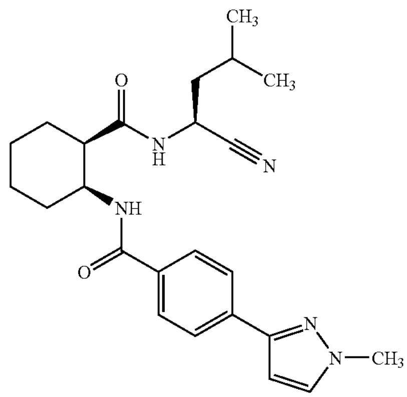 | D | N-[(1S,2R)-2-({[(1S)-1-cyano-3-methylbutyl]amino}carbonyl)cyclohexyl]-4-(1-methyl-1H-pyrazol-3-yl)benzamide |
| 68. | 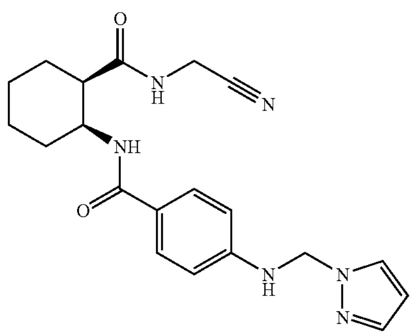 | C | N-((1S,2R)-2-{[(cyanomethyl)amino]carbonyl}cyclohexyl)-4-[(1H-pyrazol-1-ylmethyl)amino]benzamide |
| 69. | 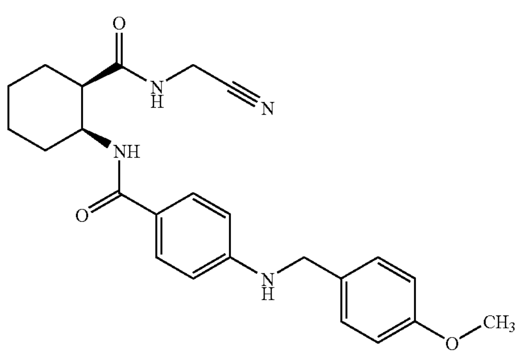 | C | N-((1S,2R)-2-{[(cyanomethyl)amino]carbonyl}cyclohexyl)-4-[(4-methoxybenzyl)amino]benzamide |
| 70. | 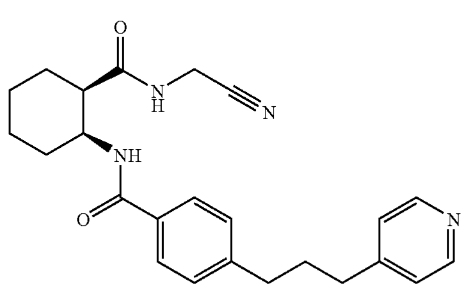 | A | N-((1S,2R)-2-{[(cyanomethyl)amino]carbonyl}cyclohexyl)-4-(3-pyridin-4-ylpropyl)benzamide |

TABLE 1-continued

| # | Structure | Method | Name |
|---|---|---|---|
| 71. | 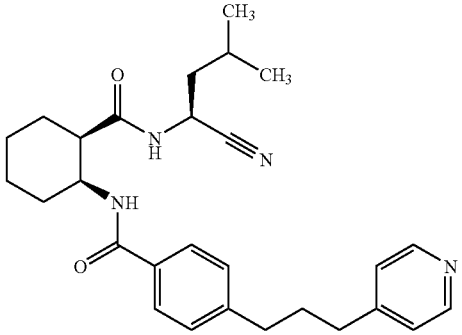 | D | N-[(1S,2R)-2-({[(1S)-1-cyano-3-methylbutyl]amino}carbonyl)cyclohexyl]-4-(3-pyridin-4-ylpropyl)benzamide |
| 72. | 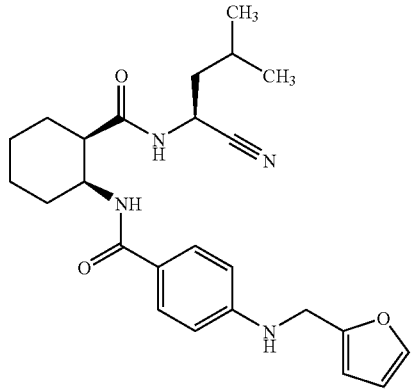 | D | N-[(1S,2R)-2-({[(1S)-1-cyano-3-methylbutyl]amino}carbonyl)cyclohexyl]-4-[(2-furylmethyl)amino]benzamide |
| 73. | 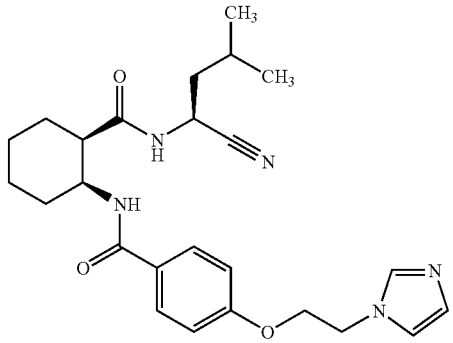 | D | N-[(1S,2R)-2-({[(1S)-1-cyano-3-methylbutyl]amino}carbonyl)cyclohexyl]-4-[2-(1H-imidazol-1-yl)ethoxy]benzamide |
| 74. | 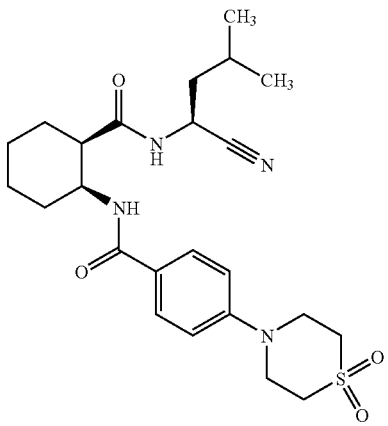 | D | N-[(1S,2R)-2-({[(1S)-1-cyano-3-methylbutyl]amino}carbonyl)cyclohexyl]-4-(1,1-dioxidothiomorpholin-4-yl)benzamide |

TABLE 1-continued
| # | Structure | Method | Name |
|---|---|---|---|
| 75. | 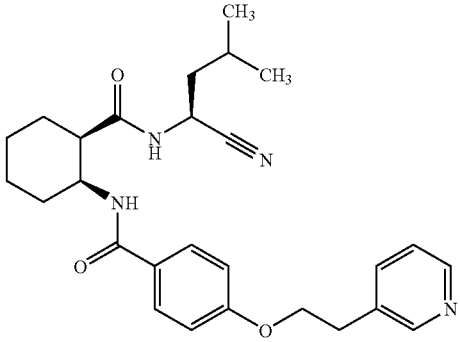 | D | N-[(1S,2R)-2-({[(1S)-1-cyano-3-methylbutyl]amino}carbonyl)cyclohexyl]-4-(2-pyridin-3-ylethoxy)benzamide |
| 76. | 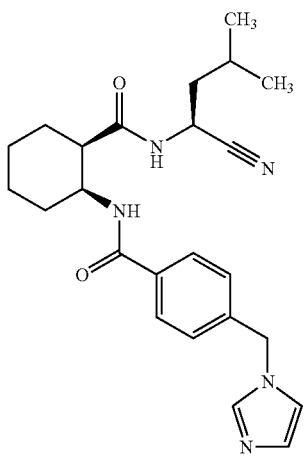 | D | N-[(1S,2R)-2-({[(1S)-1-cyano-3-methylbutyl]amino}carbonyl)cyclohexyl]-4-(1H-imidazol-1-ylmethyl)benzamide |
| 77. | 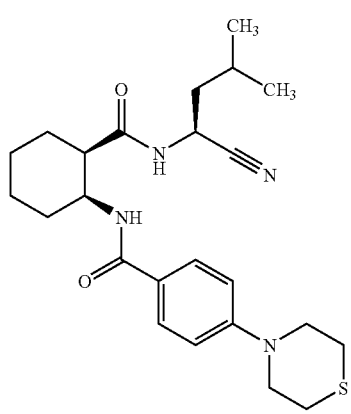 | D | N-[(1S,2R)-2-({[(1S)-1-cyano-3-methylbutyl]amino}carbonyl)cyclohexyl]-4-thiomorpholin-4-ylbenzamide |

TABLE 1-continued
| # | Structure | Method | Name |
|---|---|---|---|
| 78. | 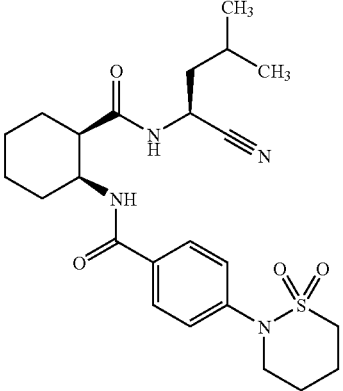 | D | N-[(1S,2R)-2-({[(1S)-1-cyano-3-methylbutyl]amino}carbonyl)cyclohexyl]-4-(1,1-dioxido-1,2-thiazinan-2-yl)benzamide |
| 79. | 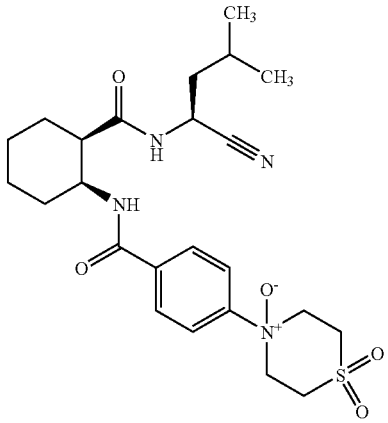 | D | N-[(1S,2R)-2-({[(1S)-1-cyano-3-methylbutyl]amino}carbonyl)cyclohexyl]-4-(1,1,4-trioxidothiomorpholin-4-yl)benzamide |
| 80. | 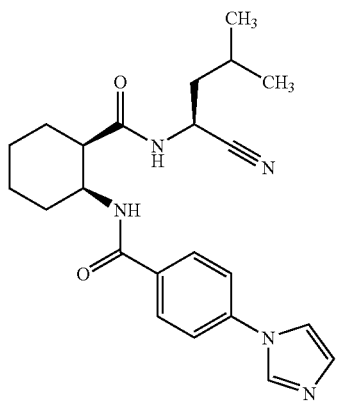 | D | N-[(1S,2R)-2-({[(1S)-1-cyano-3-methylbutyl]amino}carbonyl)cyclohexyl]-4-(1H-imidazol-1-yl)benzamide |

TABLE 1-continued

| # | Structure | Method | Name |
|---|---|---|---|
| 81. | 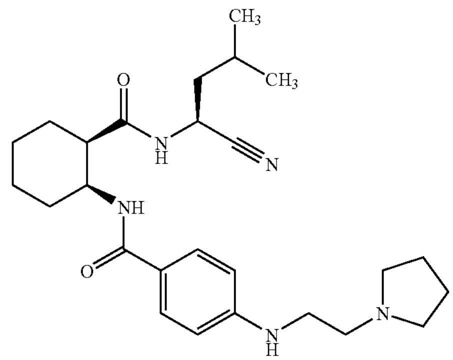 | D | N-[(1S,2R)-2-({[(1S)-1-cyano-3-methylbutyl]amino}carbonyl)cyclohexyl]-4-[(2-pyrrolidin-1-ylethyl)amino]benzamide |
| 82. | 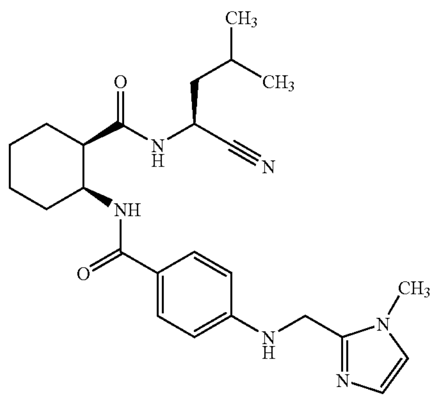 | D | N-[(1S,2R)-2-({[(1S)-1-cyano-3-methylbutyl]amino}carbonyl)cyclohexyl]-4-{[(1-methyl-1H-imidazol-2-yl)methyl]amino}benzamide |
| 83. | 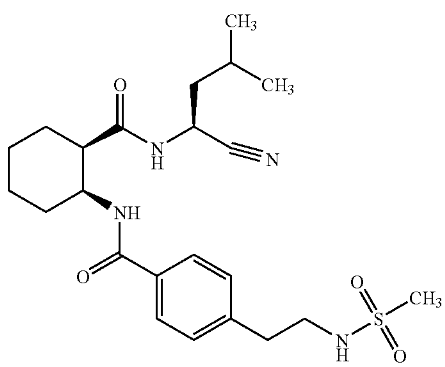 | D | N-[(1S,2R)-2-({[(1S)-1-cyano-3-methylbutyl]amino}carbonyl)cyclohexyl]-4-{2-[(methylsulfonyl)amino]ethyl}benzamide |
| 84. | 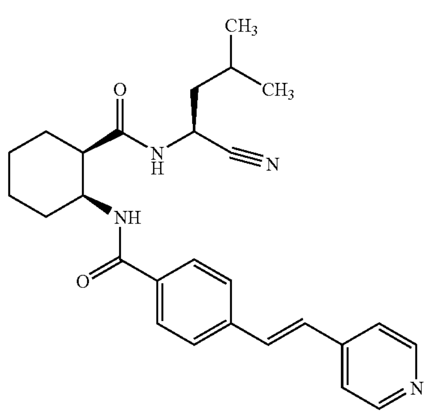 | D | N-[(1S,2R)-2-({[(1S)-1-cyano-3-methylbutyl]amino}carbonyl)cyclohexyl]-4-[(E)-2-pyridin-4-ylethenyl]benzamide |

TABLE 1-continued

| # | Structure | Method | Name |
|---|---|---|---|
| 85. | 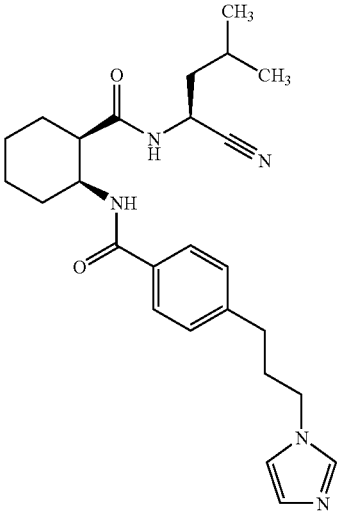 | D | N-[(1S,2R)-2-({[(1S)-1-cyano-3-methylbutyl]amino}carbonyl)cyclohexyl]-4-[3-(1H-imidazol-1-yl)propyl]benzamide |

Methods

The present invention also relates to a method for the prophylactic and/or therapeutic treatment of diseases which are associated with cysteine proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease, which method comprises administering a compound of formula (I) to a human being or an animal.

The invention also provides for the use of the aforementioned compounds for the preparation of medicaments for the treatment or prophylaxis of diseased which are associated with cysteine proteases, such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease. In one embodiment the invention relates to the use of compounds as defined above for the preparation of medicaments for the treatment or prophylaxis of osteoporosis, instable angina pectoris or plaque rupture. Such medicaments comprise a compound as defined above.

Another embodiment of the invention relates to a method for the prophylactic and/or therapeutic treatment of disorders in which cathepsin K plays a significant pathological role, such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease, which method comprises administering a compound as defined above to a human being or an animal. A preferred embodiment of the invention relates to a method for the prophylactic and/or therapeutic treatment of osteoporosis, instable angina pectoris or plaque rupture, which method comprises administering a compound as defined above to a human being or an animal.

The invention also provides combination therapies and methods comprising administering a compound of formula (I), in combination with one or more additional compounds of formula (I), or in combination with one or more additional active ingredients, to a patient or subject in need thereof. In one embodiment the combination therapy method of the invention comprises administering a compound of formula (I), in combination with a therapeutic amount of a bisphosphonic acid, bisphosphonic ester, or pharmaceutically acceptable salt thereof, to a subject or patient. Exemplary bisphosphonic acids and esters usable in combination therapies with compounds of formula (I) include, by way of example:

4-amimo-1-hydroxybutylidene-1,1-bisphosphonic acid (alendronic acid) and 4-amino-1-hydroxybutylidene-1,1-bisphosphonate monosodium trihydrate (alendronate monosodium trihydrate), described in U.S. Pat. Nos.: 4,922,007; 5,019,651; 5,510,517; and 5,648,491;

cycloheptylaminomethylene-1,1-bisphosphonic acid (cimadronic acid), described in U.S. Pat. No. 4,970,335;

1,1-dichloromethyene-1,1-diphosphonic acid (clondronic acid) and the sodium salt thereof, described in Belgian Patent No. 672,205 and in J. Org. Chem 1967, 32, 4111;

1-hydroxy-3-pyrrolidin-1-ylpropylidene-1,1-bisphosphonic acid (EB-1053);

1-hydroxyethylidene-1,1-diphosphonic acid (etidronic acid);

1-hydroxy-3-(N-methyl-N-pentylamino)propylidene-1,1-bisphosphonic acid (ibandronic acid), described in U.S. Pat. No. 4,927,814;

6-amino-1-hydroxypropylidene-1,1-bisphosphonic acid (neridronic acid)

3-(dimethylamino)-1-hydroxypropylidene-1,1-bisphosphonic acid (olpadronic acid);

3-amino-1-hydroxypropylidene-1,1-bisphosphonic acid (pamidronic acid);

2-pyrid-2-ylethylidene-1,1-bisphosphonic acid (pyridonic acid), described in U.S. Pat. No. 4,761,406;

1-hydroxy-2-pyrid-3-ylethylidene-1,1-bisphosphonic acid (risedronic acid);

4-chlorophenylsulfanylmethylenebisphosphonic acid (tiludronic acid); and 1-hydroxy-2-(1H-imidazol-1-yl)ethylidene-1,1-bisphosphonic acid (zoledronic acid).

In certain embodiments, the combination therapy may comprise administering to a patient or subject in need thereof an effective amount of a compound of formula (I) in combination with alendronic acid, cimadronic acid, clodronic acid, tiludronic acid, etidronic acid, ibandronic acid, risedronic acid, pyridronic acid, pamidronic acid, zolendronic acid, or a pharmaceutically acceptable salt or solvate thereof, and mixture thereof.

The invention further relates to a process for the manufacture or preparation of compounds of general formula (I), which process comprises:

a) reacting a compound of formula (IV)

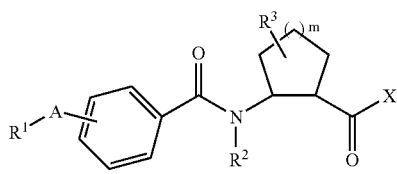

(IV)

where X is a leaving group such as halo, alkoxy or tosyl, and $R^1$, $R^2$, $R^3$, A and m are defined herein;

with a compound of formula (V)

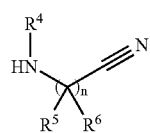

(V)

wherein $R^4$, $R^5$, $R^6$ and n are as defined herein; or b) reacting a compound of formula (VI):

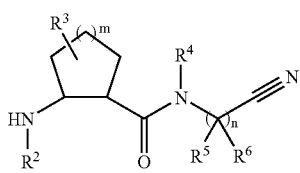

wherein $R^2$, $R^3$, $R^4$, $R^5$ and $R^6$ are as defined herein, with a compound of formula (VII)

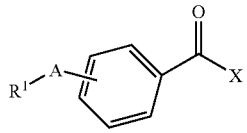

(VII)

wherein X is a leaving group and $R^1$ and A are defined herein;

to provide a compound of formula (I) above.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-20; *Rodd's Chemistry of Carbon Compounds*, Elsevier Science Publishers, 1989, Volumes 1-5 and Supplements; and *Organic Reactions*, Wiley & Sons: New York, 1991, Volumes 1-40. The following synthetic reaction schemes are merely illustrative of some methods by which the compounds of the present invention may be synthesized, and various modifications to these synthetic reaction schemes may be made and will be suggested to one skilled in the art having referred to the disclosure contained in this Application.

The starting materials and the intermediates of the synthetic reaction schemes may be isolated and purified if desired using conventional techniques, including but not limited to filtration, distillation, crystallization, chromatography, and the like. Such materials may be characterized using conventional means, including physical constants and spectral data. Unless specified to the contrary, the reactions described herein preferably take place at atmospheric pressure over a temperature range from about −78° C. to about 150° C., more preferably from about 0° C. to about 125° C., and most preferably and conveniently at about room (or ambient) temperature, e.g., about 20° C.

The invention also relates to a process as described above, which process comprises the preparation of pharmaceutically acceptable salts and/or pharmaceutically acceptable esters. The formation of the esters and/or salts can be carried out at different stages of the process, e.g. with the compound of formula (I) or with the corresponding starting materials. The reaction of a compound of formula (IV) with a compound of formula (V) can be carried out by methods known to the person skilled in the art. The reaction can conveniently be carried out by dissolving compound (IV), compound (V), TPTU (O-1,2-Dihydro-2-oxo-1-pyridyl)-N,N,N',N'-tetramethyluronium tetrafluoroborate) and Hünigs base (N-Ethyldiisopropylamine) in acetonitrile and stirring the mixture at room temperature for 6 to 16 hours. The reaction mixture can be concentrated and the product can be obtained by methods known to the person skilled in the art, e.g. by extraction and column chromatography. Alternatively, a compound of formula (IV) can be dissolved in $CH_2Cl_2$ and reacted for 6 to 16 hours at room temperature with a compound of formula (V) in the presence of N-methylmorpholine, HOBT (1-hydroxybenzotriazole hydrate) and a carboniimide such as EDCI (1-(3-dimethylaminopropyl)-3- ethylcarbodiimide hydrochloride). The product can be isolated by methods known per se, e.g. by extraction and HPLC.

The reaction of a compound of formula (IV) with a compound of formula (V) is conveniently carried out by preparing a solution of compound (IV) in $CH_2Cl_2$ and adding a solution of compound (V) in $CH_2Cl_2$. To this mixture, triethylamine is added and after shaking 6 to 16 hours at room temperature formic acid is added. The product can be isolated and purified by methods known per se, e.g. by evaporation of the solvent and HPLC.

For compounds of formula (I), it is possible to prepare the corresponding esters and/or salts starting from the compounds of formula (I) or an earlier stage, e.g. to form the corresponding salts and/or esters of the corresponding starting materials. The methods to prepare pharmaceutically acceptable salts and/or pharmaceutically acceptable esters as defined before are known in the art.

Compounds of formula (IV) are prepared by methods known to the person skilled in the art. Conveniently, a cyclic beta-amino acid such as 2-aminocyclohexanecarboxylic acid of desired stereochemistry (with the acid moiety suitably protected with a removable protecting group) may be linked to the desired benzoic acid substituted with —A—$R^1$ in a manner analogous to the methods described in the examples below. The resulting compound (II) is isolated by methods known per se, e.g. by extraction and evaporation of the solvent.

Compounds of formula (V) can conveniently be obtained by adding a solution of the corresponding aldehyde in $CH_2Cl_2$ to a solution of $NH_4Cl$ and NaCN in $H_2O$ and MeOH at 0° C. The mixture is stirred and allowed to warm to room temperature. After addition of $NH_3$ solution and completion of the reaction, the resulting compound of formula (V) is isolated and purified by methods known to the person skilled in the art, e.g. by extraction. The corresponding hydrochloride can also be prepared by methods known per se.

Chiral compounds of formula (V) can conveniently be obtained by adding ammonium bicarbonate to a mixed anhydride (prepared from a suitable t-BOC protected amino acid and di-tert-butyl dicarbonate) at 15° C. The reaction mixture is stirred at room temperature for 1-5 h. After completion of the reaction the resulting t-BOC protected amino acid amide is isolated and purified by methods known to the person skilled in the art, e.g. by extraction. The Boc protected amino acid amide and triethylamine are dissolved in THF and trifluoroacetic acid anhydride at 0° C. The mixture is stirred for 2 h at −10° C. After isolation and purification of the resulting intermediate product, e.g. by evaporation of the solvent and flash chromatography, the t-BOC protective group can be cleaved off with HCl in acetic acid to yield the desired compound of formula (V).

Compounds of formula (VI) can conveniently be obtained by reacting the corresponding t-BOC protected amino acid with a compound of formula (V) analogous to the method described above. After isolation and purification of the resulting intermediate product, e.g. by evaporation of the solvent and flash chromatography, the t-BOC protective group can be cleaved off with trifluoro-acetic acid to yield the desired compound of formula (VI) with trifluoro-acetic acid.

Compounds of formula (VI) are either commercially available or can be obtained by conventional methods well known in the art.

The present invention relates to all compounds of formula (I), as prepared by one of the processes described above.

Administration and Pharmaceutical Composition

The invention includes pharmaceutical compositions comprising a compound as defined above and a pharmaceutically acceptable carrier and/or adjuvant or diluent. The compositions are for use in context with diseases associated with cysteine proteases such as osteoporosis, osteoarthritis, rheumatoid arthritis, tumor metastasis, glomerulonephritis, atherosclerosis, myocardial infarction, angina pectoris, instable angina pectoris, stroke, plaque rupture, transient ischemic attacks, amaurosis fugax, peripheral arterial occlusive disease, restenosis after angioplasty and stent placement, abdominal aortic aneurysm formation, inflammation, autoimmune disease, malaria, ocular fundus tissue cytopathy and respiratory disease. In one embodiment the invention relates to pharmaceutical compositions comprising a compound as defined above and a pharmaceutically acceptable carrier and/or adjuvant for use in context with osteoporosis, instable angina pectoris or plaque rupture.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as a severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms.

The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 9th edition, Easton, Pa. Representative pharmaceutical formulations containing a compound of the present invention are described in the following examples.

EXAMPLES

The following examples and preparations are provided to enable those skilled in the art to more clearly understand and to practice the present invention. They should not be considered as limiting the scope of the invention, but merely as being illustrative and representative thereof. The starting materials used in the examples and preparations are either commercially available or can be obtained by methods known in the art (e.g. from: DE 26 24 290; WO 98/0354; Chem. Pharm. Bull., 38(2), 350-354 (1990), Chiral Synthon Obtained with Pig Liver Esterase: Introduction of Chiral Centers into Cyclohexene Skeleton; J. Chem. Soc. Perkin Trans., 1, 1411-1415 (1994), Asymmetric Synthesis of (-)-(1R, 2S)-Cispentacin and Related cis- and trans-2-Amino Cyclopentane- and Cyclohexane-1-carboxylic Acids) or can be obtained by methods analogous to the methods described before. Table 2 provides a list of acronyms for reagents and solvents used in the following examples.

TABLE 2

| | |
|---|---|
| Burgess Reagent | (Methoxycarbonylsulfamoyl)triethylammonium hydroxide, inner salt |
| DCM, CH2Cl2 | Dichloromethane |
| DIC | 2-Dimethylaminoisopropyl chloride hydrochloride |
| DIPEA | N,N-Diisopropylethylamine |
| DMAP | 4-Dimethylaminopyridine |
| DMF | N,N-Dimethylformamide |
| EDCl | 1-(3-Dimethylaminopropyl)-3-ethylcarbodiimide hydrochloride |
| HOBT | 1-Hydroxybenzotriazole hydrate |
| MEOH | Methanol |
| NMM | N-Methylmorpholine |
| NMP | 1-Methyl-2-pyrrolidinone |
| TBS | tert-Butyldimethylsilyl protecting group |
| TFA | Trifluoroacetic acid |
| THF | Tetrahydrofuran |

A. Preparation of Cyclopropylglycine Amides and Nitriles

Preparation 1

R,S-Cyclopropylaminonitrile

R,S-Cyclopropylaminonitrile was prepared according to Gabriel, Tobias; Pech, Michael; Rodriguez Sarmiento, Rosa Maria, PCT publication No. WO 01/96285.

Preparation 2

(S)-Cyclopropylglycine amide

Step 1

(S)-Cyclopropylglycine methyl ester

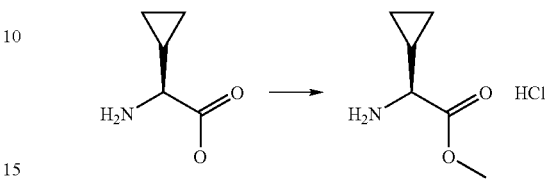

To a 0° C. solution of thionyl chloride (7.6 mL, 104 mmol) in anhydrous methanol (750 mL) was added (S)-cyclopropylglycine (10.0 g, 86.9 mmol, Eastman Chemical Company, Kingsport, Tenn.). The reaction mixture was allowed to warm to room temperature and then refluxed for 4 hrs, then cooled to room temperature and concentrated in vacuo to give a crude solid. The solids were washed with acetone to give 8.94 g of (S)-cyclopropylglycine methyl ester HCl as a white solid. Yield: 62%, MS: 130 (M+H$^+$), mp=134.0-135.9° C.

Step 2

(S)-Cyclopropylglycine amide

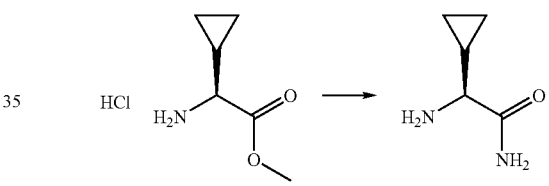

To a 0° C. solution of ammonia in methanol (100 mL, 7M) in a bomb was added (S)-cyclopropylglycine methyl ester HCl (5.04 g, 30.4 mmol). The bomb was sealed and placed in a 70° C. oil bath for two days. The reaction mixture was cooled to room temperature and concentrated until a suspension formed. The suspension was filtered and the collected solids were washed with methanol:acetone (1:1). Another crop of solids was obtained from the mother liquor in this manner, and the combined solids were dried to give 3.52 g of the product as a white powder. Yield: 100%, MS: 115 (M+H$^+$), mp=225.0-231.0° C., $[\alpha]_D^{25}$=+63.0 (1.00, 1M HCl).

Preparation 3

(S)-Cyclopropylglycine nitrile

Step 1

2-(2-Hydroxy-2-phenyl-ethylamino)-3-methyl-pentanenitrile

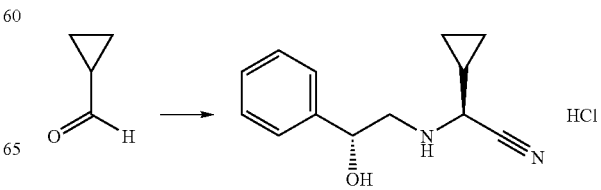

To a solution of cyclopropylcarboxyaldehyde (10.27 g, 146.5 mmol) in 500 mL of anhydrous methylene chloride was added (R)-phenylglycinol (20.06 g, 146.2 mmol). The reaction mixture was stirred at room temperature for 2 h, then cooled to −26° C. with a dry ice/acetone bath. Trimethylsilyl cyanide (39.0 mL, 292 mmol) was slowly added via syringe keeping the reaction temperature below −23° C. The reaction mixture was allowed to warm to room temperature and stirred overnight. 100 mL of methanol and 150 mL of 1M HCl were added and the reaction mixture was stirred for 1 h. The reaction mixture was neutralized with 150 mL of 1M sodium hydroxide, the organic layer separated and washed with 400 mL of water, dried over sodium sulfate, filtered and concentrated to give a yellow liquid. The product was isolated as the monohydrochloride salt by treating the free amine in methylene chloride with 1M HCl in ether to give 34.24 g of 2-(2-Hydroxy-2-phenyl-ethylamino)-3-methyl-pentanenitrile as a white solid (with an 83:17 S:R ratio at the glycine stereocenter, as determined by $^1$H NMR spectroscopy) mixture of diastereomers. Yield: 93%, MS: 217 (M+H$^+$), mp=106.0-108.1° C.

Step 2

(S)-Cyclopropylglycine nitrile

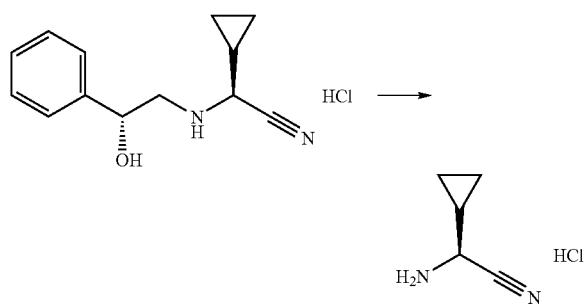

To a 0° C. solution of the glycinol adduct of step 1 (5.00 g, 19.8 mmol) in 70 mL of methanol and 35 mL of methylene chloride was added lead tetracetate (9.15 g, 20.6 mmol) portionwise over a 1 minute period. The reaction mixture was stirred for 30 minutes at 0° C. and the resulting suspension was filtered through a pad of celite. The collected solids were washed with 2×100 mL of methylene chloride and the organic layer was separated, washed with 200 mL of water, dried over sodium sulfate, filtered and concentrated to the imine (3.55 g, 97%) as a clear liquid. The imine was directly hydrolyzed to give cyclopropylglycine nitrile by dissolving in ether and treating with 1M HCl in an ice bath. The hydrolysis was followed by TLC by monitoring for the disappearance of the imine (Rf=0.43, 10:90 EtOAc:hexanes). After complete hydrolysis, the aqueous layer was separated, washed with ether, then carefully concentrated on the rotary evaporator (30-42° C. water bath) and concentrated in vacuo to give (S)-cyclopropylglycine nitrile as a hygroscopic white solid B. Preparation of Carboxylic Acids Preparation 4

4-[(5-methyl-thiophen-2-ylmethyl)-amino]-benzoic acid

4-[(5-methyl-thiophen-2-ylmethyl)-amino]-benzoic acid, as well as the other benzoic acids noted below, were prepared by reductive amination of the corresponding methyl 4-aminobenzoate followed by hydrolysis.

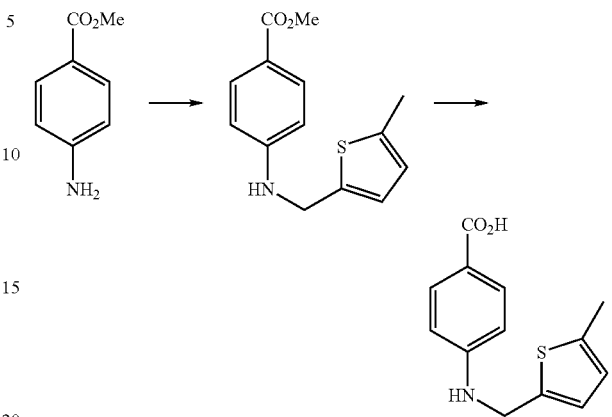

To a mixture of 200 mg (1.32 mmol) methyl 4-aminobenzoate and 167 mg (1.32 mmol) 5-methyl-2-thiophenecarboxaldehyde dissolved in 8 mL dichloromethane was added 420 mg (1.98 mmol) sodium triacetoxyborohydride. The mixture was stirred at room temperature overnight, then partitioned between ethyl acetate and water, dried over magnesium sulfate and concentrated. Column chromatography, eluting with 20% ethyl acetate/hexane, provided 316 mg (1.2 mmol) of 4-[(5-Methyl-thiophen-2-ylmethyl)-amino]-benzoic acid methyl ester. This product was then dissolved in 10 mL methanol and treated with 127 mg (3.0 mmol) of lithium hydroxide dissolved in 5 mL water. The mixture was stirred at room temperature overnight, then partitioned between ethyl acetate and 1 N HCl, dried over magnesium sulfate and concentrated to provide 276 mg (92% yield) of 4-[(5-methyl-thiophen-2-ylmethyl)-amino]-benzoic acid (used in preparation of compound 64 of Table 1) as a pale yellow solid.

The above procedure was employed to provide the following acids for use in preparing various compounds of Table 1 as indicated by the compound numbers:

4-[(pyridin-3-ylmethyl)-amino]-benzoic acid (compound 63);

4-[(thiazol-2-ylmethyl)-amino]-benzoic acid (compound 66)

4-[(pyrazol-1-ylmethyl)-amino]-benzoic acid (compound 68);

4-[(furan-2-ylmethyl)-amino]-benzoic acid (compound 72); and

4-[(1-Methyl-1H-imidazol-2-ylmethyl)-amino]-benzoic acid (compound 82)

Preparation 5

The following acids were prepared by nucleophilic displacement of methyl 4-fluorobenzoate by amines according to the procedure reported in WO 01/58886, followed by hydrolysis to the corresponding carboxylic acids as described above:

4-(4-Propyl-piperazin-1-yl)-benzoic acid (compound 25 and 26);

4-(4-Isopropyl-piperazin-1-yl)-benzoic acid (compound 27 and 28);

4-(4-Methyl-piperazin-1-yl)-benzoic acid (compound 33);

4-(4-Benzyl-piperazin-1-yl)-benzoic acid (compound 36);

4-(2-Morpholin-4-yl-ethylamino)-benzoic acid (compound 46); and 4-(2-Pyrrolidin-1-yl-ethylamino)-benzoic acid (compound 81).

Preparation 6

4-[1-(2-methoxyethyl)-piperidin-4-yl]-benzoic acid hydrochloride, 4-[1-(2-ethyl)-piperidin-4-yl]-benzoic acid hydrochloride, and 4-[1-(2-propyl)-piperidin-4-yl]-benzoic acid hydrochloride, employed for compounds 34, 35, 48 and 50 of Table 1 respectively, were prepared according to the procedure reported in WO 01/58886, followed by hydrolysis to the corresponding carboxylic acid as described above.

Preparation 7

The following acids were prepared according to the procedure reported in WO 00/48993 and used for preparation of the indicated compounds:

4-(6-Methyl-pyridin-3-yloxy)-benzoic acid (compound 52);

4-(5-Methyl-pyridin-3-ylmethyl)-benzoic acid (compound 53);

4-(3-Pyridin-3-yl-propyl)-benzoic acid (compound 65); and 4-(3-Pyridin-4-yl-propyl)-benzoic acid (compound 70and 71).

Preparation 8

The substituted benzoic acids used in preparation of compounds 31, 37 and 38 of Table 1 were prepared according to the procedure reported in *Synlett* 2000, No. 6, 829.

Preparation 9

4-(2H-Pyrazol-3-yl)-benzoic acid (used for compounds 59 and 62) was prepared using the procedure outlined by Almirante, N., Cerri; A., Fedrizzi; G., Marazzi; G., Santagostino. *Tetrahedron Lett.,* 1998, 39, 3287).

Preparation 10

4-Imidazol-1-ylmethyl-benzoic acid, used for compound 76, was prepared according to the procedure reported in Journal of Medicinal Chemistry 1987, 30(8), 1342-7.

Preparation 11

4-(1,1-Dioxo-1lambda$^6$-[1,2]thiazinan-2-yl)-benzoic acid, used for compound 78, was prepared according to Journal de la Societe Algerienne de Chimie 1994, 4(2), 171-7.

Preparation 12

4-(2-Methanesulfonylamino-ethyl)-benzoic acid, used for compound 83, was prepared according to DE 3000377.

Preparation 13

4-(2-Pyridin-4-yl-vinyl)-benzoic acid, used for compound 84, was prepared according to DE 4326344.

Preparation 14

4-(3-Imidazol-1-yl-propyl)-benzoic acid, used for compound 85, was prepared according to the procedure reported by Journal of Medicinal Chemistry 1981, 24(10), 1139-48.

Preparation 15

4-(3-Methyl-3H-imidazol-4-yl)-benzoic acid

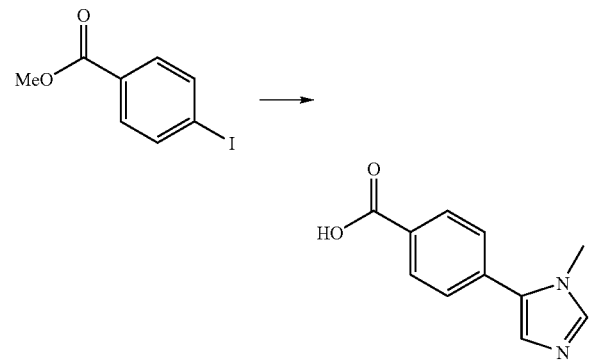

4-(3-Methyl-3H-imidazol-4-yl)-benzoic acid methyl ester was prepared using the procedure similar to that outlined by Pivsa-Art, S.,; Satoh, T., Kawamura, Y., Miura, M., Nomura, M. *Bull. Chem. Soc. Jpn.* 71, 1998, 467. In a flask was dried $Cs_2CO_3$ (3.29 g, 12 mmol) in vacuo at 150° C. for 1.5 hr. After cooling to ambient temperature, N-methylimidazole (0.5 mL, 6 mmol), methyl-4-iodo-benzoate (3.29 g, 12 mmmol), $Pd(OAc)_2$ (0.14 g, 0.6 mmol), $PPh_3$ (4.09 g, 12 mmol), and 20 mL dimethylformamide. The mixture was stirred under nitrogen at 140° C. for 24 hrs and an additional 16 hrs at ambient temperature. The mixture was poured onto 10% aqueous NaOH and extracted with $CH_2Cl_2$, dried over $Na_2SO_4$. Purification by chromatography (5% MeOH/$CHCl_3$) gave 0.50 g (37%) of 4-(3-methyl-3H-imidazol-4-yl)-benzoic acid methyl ester. A solution of 4-(3-methyl-3H-imidazol-4-yl)-benzoic acid methyl ester (216 mg, 1 mmol), lithium hydroxide (44.0 mg, 1 mmol), tetrahydrofuran (0.6 mL), water (0.6 mL), and methanol (0.6 mL) was stirred at ambient temperature under nitrogen for 24 hrs. The mixture was concentrated in vacuo and then lyophilized to give 242 g of crude material which was taken on without further purification for preparation of compound 42 of Table 1.

Preparation 16

4-(2-Methyl-thiazol-4-yl)-benezoic acid

-continued

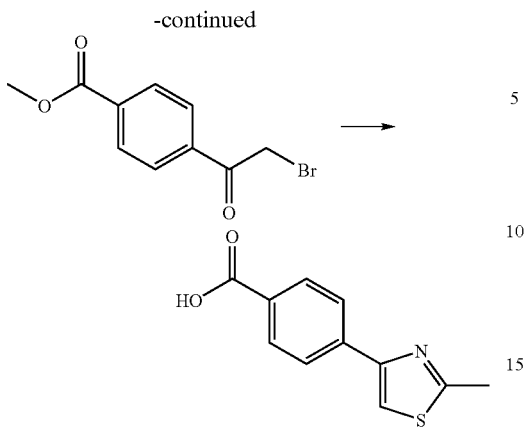

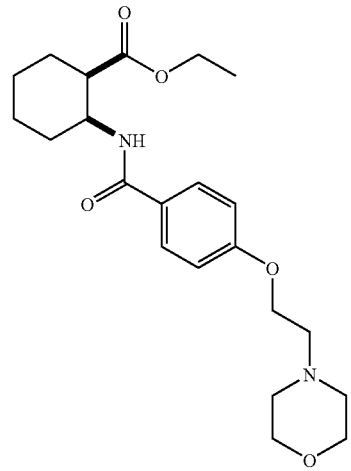

A mixture of methyl-4-acetylbenzoate (7.59 g, 43 mmol) and acetic acid (100 mL) was heated to 70° C. The reaction was cooled to 30° C. once the benzoate was dissolved. Bromine (2.2 mL, 43 mmol) was added dropwise over a period of 30 mins. The reaction was stirred at ambient temperature under nitrogen for 19 hrs. Precipitates formed upon cooling with an ice bath. The precipitate was filtered and washed with a cold solution of 1:1 MeOH/H$_2$O. The crude material (5.05 g) was taken to the next reaction without further purification. A solution of 4-bromoacetyl-benzoic acid methyl ester (0.50 g, 1.9 mmol), ethanol (6.5 mL), and thioacetamide (0.29 mg, 3.9 mmol) was refluxed under nitrogen for 5 hrs. After cooling, the reaction was poured onto water (75 mL) and stirred for 10 mins. The precipitate was filtered and washed with water. The product was collected as a pale yellow powder 0.43 g (95%). A solution of 4-(2-methyl-thiazol-4-yl)-benzoic acid methyl ester (400 mg, 1.7 mmol), lithium hydroxide (108 mg, 2.6 mmol), tetrahydrofuran (2 mL), water (2 mL), and methanol (1.5 mL) was stirred at ambient temperature under nitrogen for 16 hrs. The reaction was concentrated, diluted with water (10 mL), acidified with HCl (4 mL, 1M), and extracted with ethyl acetate and methylene chloride. The organic layers were combined, dried on sodium sulfate, and concentrated to give 0.35 g (94%) of 4-(2-methyl-thiazol-4-yl)-benzoic acid, which was used in the preparation of compound 47 of Table 1.

Preparation 17

Ethyl (1R,2S)-2-{[4-(2-morpholin-4-ylethoxy)benzoyl]amino}cyclohexanecarboxylate

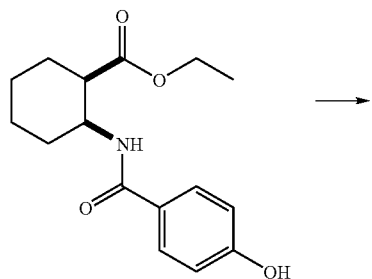

A solution of 200 mg ethyl (1R,2S)-2-[(4-hydroxybenzoyl)amino] cyclohexanecarboxylate in 5 mL DMF was treated with 1 g of potassium carbonate followed by 500 mg of N-(2-chloroethyl)morpholine hydrochloride. Under nitrogen atmosphere and with magnetic stirring, the reaction was heated to 100 C. for 8 hr, then stirred at 50° C. for 5 days. After cooling, the reaction was diluted with ethyl acetate and washed with water and brine. The aqueous layers were extracted twice with ethyl acetate. The combined organic layers were dried using magnesium sulfate, then filtered and solvent removed to provide ethyl (1R,2S)-2-{[4-(2-morpholin-4-ylethoxy)benzoyl]amino}cyclohexanecarboxylate.
The material was carried on for use in preparation of compounds 14 and 15 of Table 1.

Preparation 18

N-((1S,2R)-2-{[(cyanomethyl)amino]carbonyl}cyclohexyl)-4-{[(pyridin-4-ylmethyl)amino]sulfonyl}benzamide

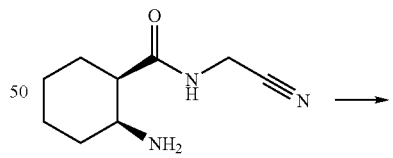

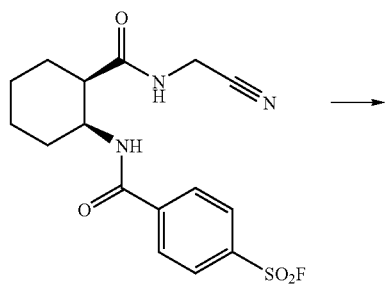

-continued

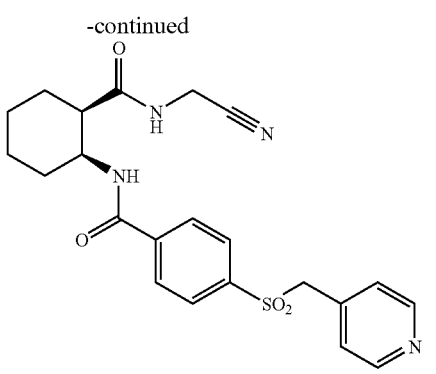

To a solution of 912 mg (5.03 mmol) (1R,2S)-2-amino-N-(cyanomethyl)cyclohexanecarboxamide (prepared according to method C) and 895 uL (11.07 mmol) pyridine dissolved in 10 mL dichloromethane was added 1.12 g (5.03 mmol) 4-(fluorosulfonyl)benzoyl chloride. The mixture was stirred for 30 minutes, partitioned between dichloromethane and 1 N HCl, dried over magnesium sulfate and concentrated to provide 1.54 g (84% yield) of crude product, pure by $^1$H NMR. To a mixture of 100 mg (0.272 mmol) of the above crude N-((1S,2R)-2-{[(cyanomethyl)amino]carbonyl}cyclohexyl)-4fluorobenzamide and 114 uL (0.817 mmol) triethylamine dissolved in 5 mL dichloromethane was added 88 mg (0.817 mmol) 4-picolylamine. The mixture was stirred at room temperature for 3 days, partitioned between ethyl acetate and water, dried over magnesium sulfate and concentrated. Column-chromatography, eluting with 20:1 dichloromethane:methanol provided 59 mg (48% yield) of N-((1S,2R)-2-{[(cyanomethyl)amino]carbonyl}cyclohexyl)-4-{[(pyridin-4-ylmethyl)amino]sulfonyl}benzamide, which was used in the preparation of compound 58 of Table 1.

Example 1

Example of Method A

Synthesis of N-((1S,2R)-2-{[(cyanomethyl)amino]carbonyl}cyclohexyl)-1,1'-biphenyl-4-carboxamide

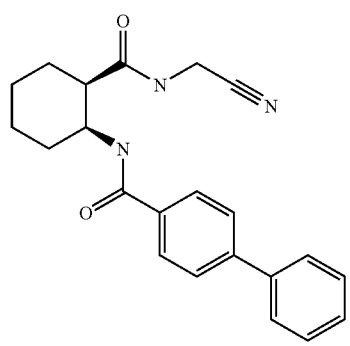

Step 1

Ethyl (1R,2S)-2-]( 1,1'-biphenyl-4-ylcarbonyl)amino]cyclohexanecarboxylate

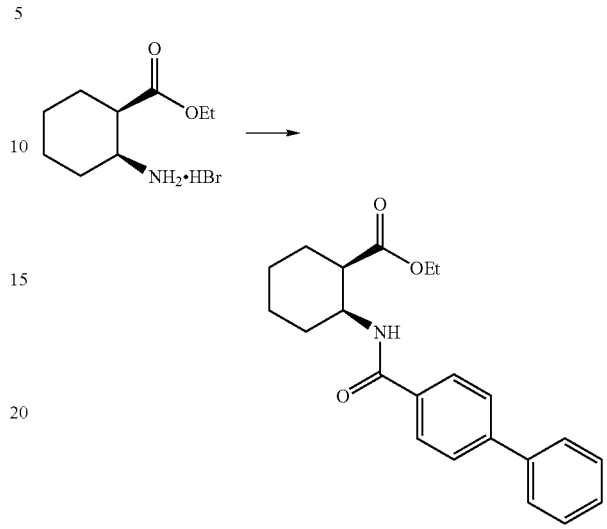

To 191 mg (0.76 mmol) of ethyl (1R,2S)-2-aminocyclohexanecarboxylate HBr salt (Xu, Daquiang et al., *Tetrahedron:Asymmetry* (1988), 9(10) 1635) dissolved in 6 mL DMF was added 150 mg (0.76 mmol) of 4-biphenylcarboxylic acid, 145 mg (0.76 mmol) of EDCI, 102 mg (0.76 mmol) of HOBT and 0.291 mL (2.65 mmol) of N-methylmorpholine. The reaction mixture was stirred at room temperature overnight, partitioned between ethyl acetate and water, dried over magnesium sulfate and concentrated to provide the crude ethyl (1R,2S)-2-](1,1'-biphenyl-4-ylcarbonyl)amino]cyclohexanecarboxylate.

Step 2

(1R,2S)-2-](1,1'-biphenyl-4-ylcarbonyl)amino]cyclohexanecarboxylic acid

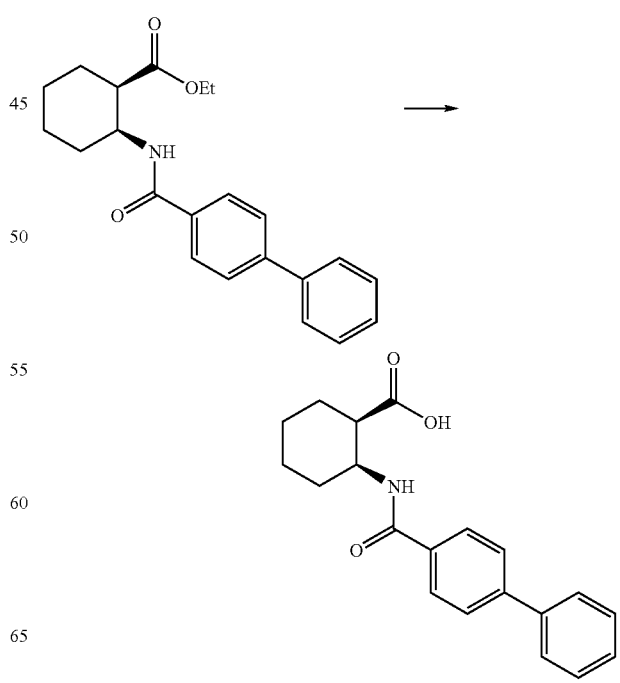

The crude reaction mixture of step 1 was dissolved in 10 mL methanol, and 79 mg (1.88 mmol) of lithium hydroxide dissolved in 2 mL water was added. The reaction mixture was stirred overnight, partitioned between dichloromethane and 1 N HCl, dried over magnesium sulfate and concentrated to provide 242 mg of (1R,2S)-2-](1,1'-biphenyl-4-ylcarbonyl)amino]cyclohexanecarboxylic acid.

Step 3

N-((1S,2R)-2-{[(cyanomethyl)amino]carbonyl}cyclohexyl)-1,1'-biphenyl-4-carboxamide

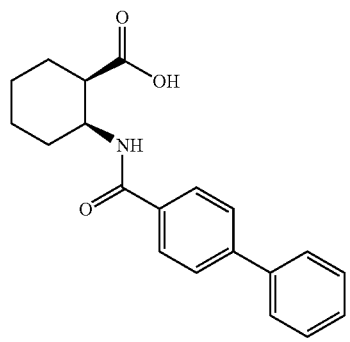

To 242 mg (0.75 mmol) of the above acid dissolved in 5 mL DMF was added 69 mg (0.75 mmol) aminoacetonitrile hydrochloride, 143 mg (0.75 mmol) of EDCI, 101 mg (0.75 mmol) of HOBT and 0.288 mL (2.62 mmol) of N-methylmorpholine. The reaction mixture was stirred at room temperature overnight, partitioned between ethyl acetate and water, dried over magnesium sulfate and concentrated. Column chromatography, eluting with 10% acetone in dichloromethane, provided 188 mg of the title compound N-((1S,2R)-2-{[(cyanomethyl)amino]carbonyl}cyclohexyl)-1,1'-biphenyl-4-carboxamide.

Additional compounds prepared by the above method are shown in Table 1.

Example 2

Example of Method B

Synthesis of N-[(1S,2R)-2-({[(1S)-1-cyano-3-methylbutyl]amino}carbonyl)cyclohexyl]-4-(4-propylpiperazin-1-yl)benzamide

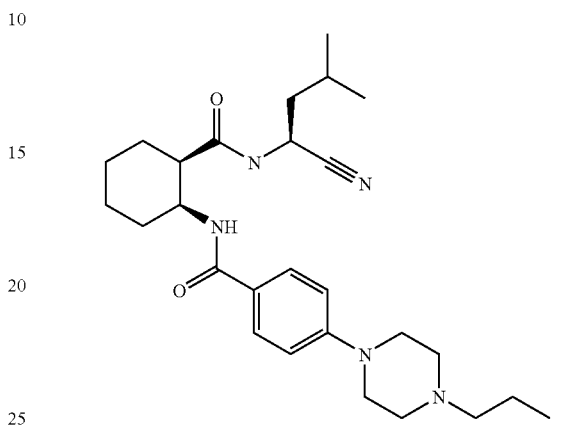

Step 1

N-[2-(1-Carbamoyl-3-methyl-butylcarbamoyl)-cyclohexyl]-4-(4-propyl-piperazin-1-yl)-benzamide

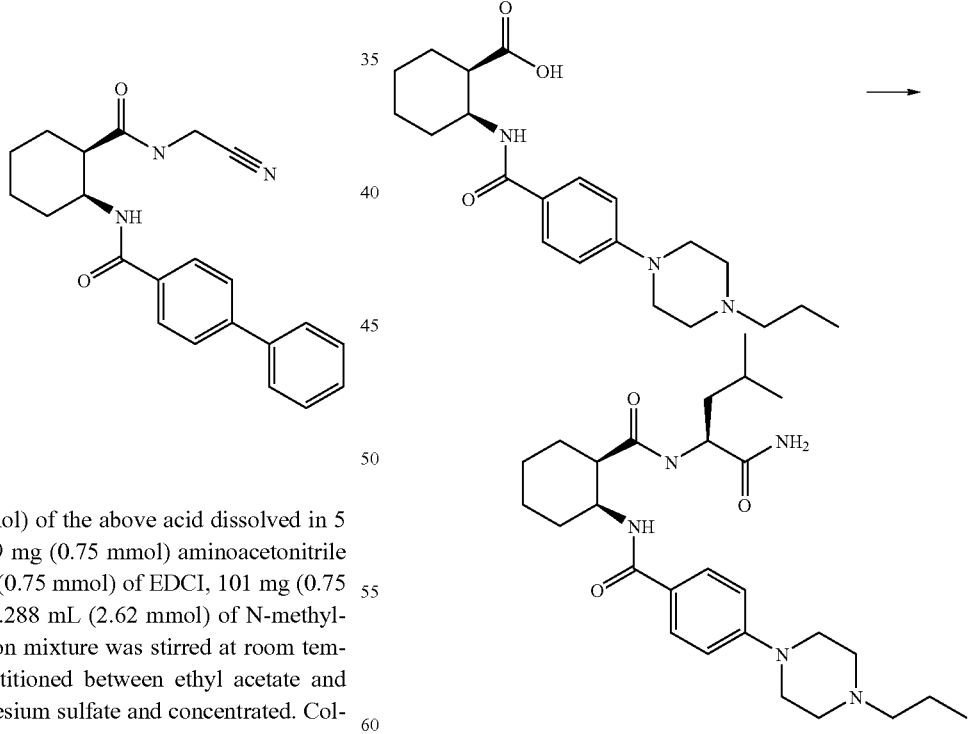

(1R,2S)-2-{[4-(4-Propylpiperazin-1-yl)benzoyl]amino}cyclohexanecarboxylic acid was prepared as described in Method A above. The 4-(4-proplypiperazin-1-yl)benzoic acid precursor was prepared according to the procedure reported in WO 01/58886. To 200 mg (0.54 mmol) of this acid dissolved in 5 ml DMF was added 89 mg (0.54 mmol) of L-leucinamide hydrochloride, 73 mg (0.54 mmol) of HOBT, 104 mg (0.54 mmol) of EDCI and 0.208 ml (1.89 mmol) of N-methylmorpholine. The reaction mixture was stirred at room temperature overnight, partitioned between ethyl acetate and water, dried over magnesium sulfate and concentrated to give the crude product as a white solid.

Step 2

N-[(1S,2R)-2-({[(1S)-1-cyano-3-methylbutyl]amino}carbonyl)cyclohexyl]-4-(4-propylpiperazin-1-yl)benzamide

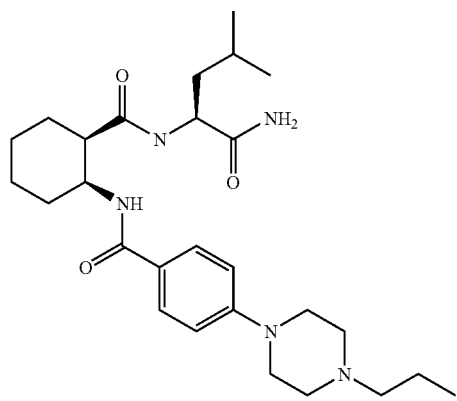

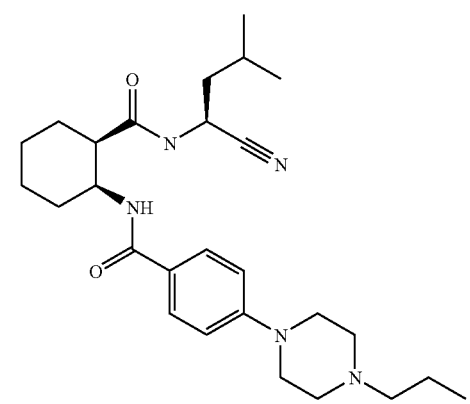

To a 0° C. solution of the amide and anhydrous pyridine (4 mL) was added trifluroacetic anhydride (0.153 ml, 1.08 mmol) dropwise. The reaction mixture was stirred for 20 mins. at 0° C., then 15 mL of 1M aqueous HCl was added slowly. The product was extracted into ethyl acetate, washing with 1M aqueous HCl until the aqueous layer remained acidic. The organic layer dried with magnesium sulfate, and concentrated. Column chromatography, eluting with 20:1 dichloromethane:methanol, gave the title compound (75 mg) as an off-white solid.

Additional compounds prepared by the above method are shown in Table 1.

Example 3

Example of Method C

Synthesis of N-((1S,2R)-2-{[(cyanomethyl)amino]carbonyl}cyclohexyl)-4-[1-(2-methoxyethyl)piperidin-4-yl]benzamide

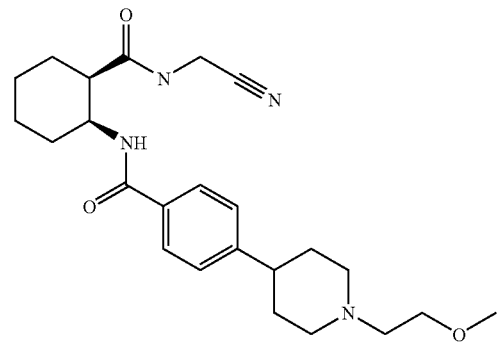

Step 1

Ethyl (1R,2S)-2-[(tert-butoxycarbonyl)amino]cyclohexanecarboxylate

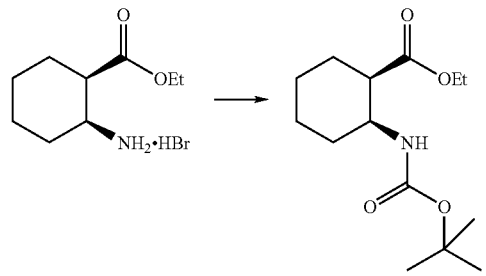

To 6.0 g (23.79 mmol) of ethyl (1R,2S)-2-aminocyclohexanecarboxylate HBr dissolved in 30 mL THF and 3.25 mL (23.79 mmol) of triethylamine was added 5.71 g (23.79 mmol) di-tert-butyl dicarbonate. The reaction mixture was stirred at room temperature overnight, partitioned between ethyl acetate and water, dried over magnesium sulfate and concentrated to provide 6.05 g of the crude ethyl (1R,2S)-2-[(tert-butoxycarbonyl)amino]cyclohexanecarboxylate.

Step 2

(1R,2S)-2-[(tert-butoxycarbonyl)amino]cyclohexanecarboxylic acid

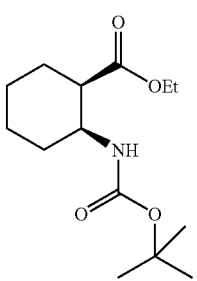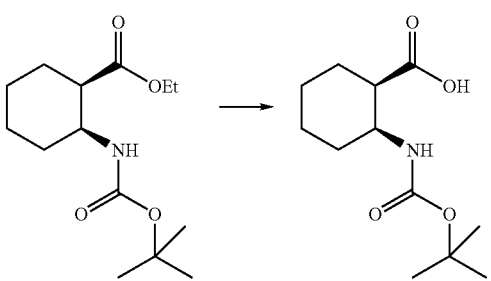

To 6.05 grams (22.3 mmol) of the ester of step 1 dissolved in 25 mL methanol was added 2.6 g (55.74 mmol) lithium hydroxide monohydrate dissolved in 10 mL water. The mixture was stirred for 48 hours, partitioned between ethyl acetate and 1 N HCl, dried over magnesium sulfate and concentrated to obtain 5.05 g of the crude (1R,2S)-2-[(tert-butoxycarbonyl)amino]cyclohexanecarboxylic acid.

Step 3 tert-Butyl (1S,2R)-2-{[(cyanomethyl)amino]carbonyl}cyclohexylcarbamate

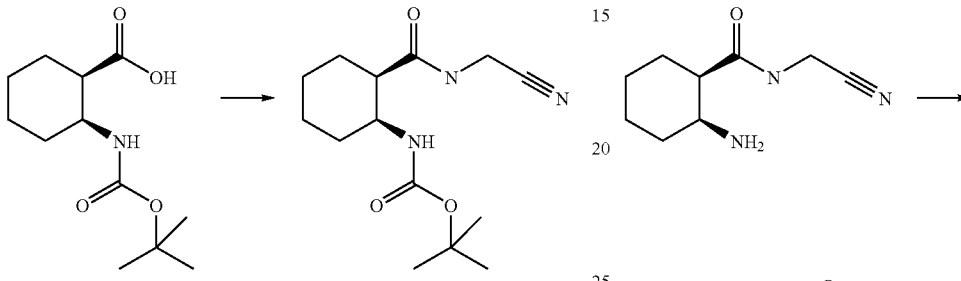

To 5.05 g (20.75 mmol) of the acid of step 2 dissolved in 40 mL DMF was added 1.92 g (20.75 mmol) aminoacetonitrile hydrochloride, 3.98 g (20.75 mmol) of EDCI, 2.80 g (20.75 mmol) of HOBT and 7.98 mL (72.63 mmol) of N-methylmorpholine. The reaction mixture was stirred at room temperature overnight, partitioned between ethyl acetate and water, dried over magnesium sulfate and concentrated to obtain 5.83 g of the crude tert-butyl (1S,2R)-2-{[(cyanomethyl)amino]carbonyl}cyclohexylcarbamate.

Step 4

(1R,2S)-2-Amino-N-(cyanomethyl)cyclohexanecarboxamide

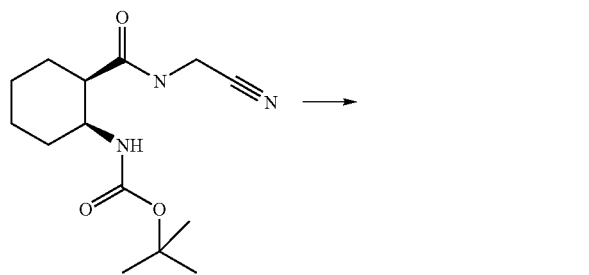

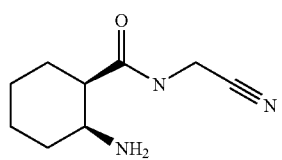

The nitrile compound of step 3 (5.82 g, 20.68 mmol) was dissolved in 69 mL (0.3M) of formic acid and stirred at room temperature for 5 h to completion. The formic acid was evaporated and the residue partitioned between ethyl acetate and 1 N sodium hydroxide, repeating the extraction three times with fresh ethyl acetate. The organic layers were combined, dried over magnesium sulfate and concentrated to give 2.22 g of the crude (1R,2S)-2-amino-N-(cyanomethyl)cyclohexanecarboxamide.

Step 5

N-((1S,2R)-2-{[(cyanomethyl)amino]carbonyl}cyclohexyl)-4-[1-(2-methoxyethyl)piperidin-4-yl]benzamide

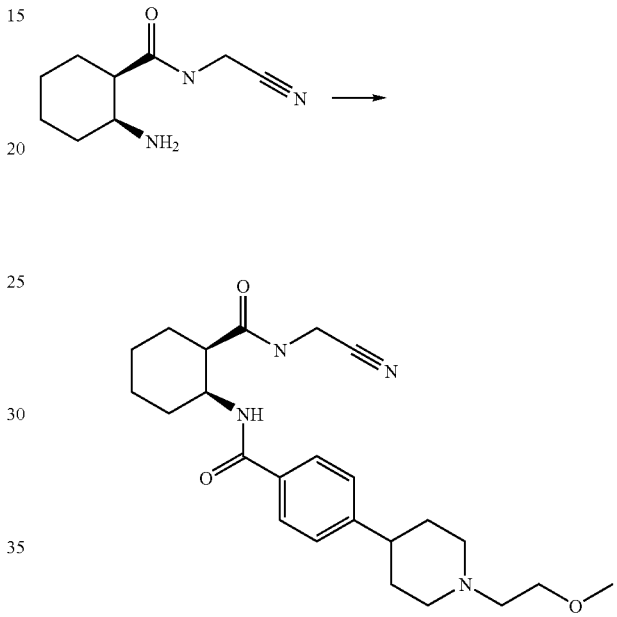

To 105 mg (0.58 mmol) of the amine from step 3 dissolved in 10 mL DMF was added 175 mg (0.58 mmol) of 1-(2-methoxyethyl)piperidin-4-yl]benzoic acid (this acid was prepared according to the procedure described in PCT Int. Appl. WO 01/58886), 110 mg (0.58 mmol) of EDCI, 78 mg (0.58 mmol) of HOBT and 0.22 mL (2.02 mmol) of N-methylmorpholine. The reaction mixture was stirred at room temperature overnight, partitioned between ethyl acetate and water, dried over magnesium sulfate and concentrated. Column chromatography, eluting with 10% methanol in dichloromethane provided 27.8 mg of the title compound N-((1S,2R)-2-{[(cyanomethyl)amino]carbonyl}cyclohexyl)-4-[1-(2-methoxyethyl)piperidin-4-yl]benzamide.

In a similar manner, allyl 4-({4-[4-({[(1S,2R)-2-({[cyano(cyclopropyl)methyl]amino}carbonyl)cyclohexyl]amino}carbonyl)phenyl]-1,3-thiazol-2-yl}amino) piperidine-1-carboxylate was prepared, using Alloc-protected piperidinylamino-5H-thiazol benzoic acid prepared as described by Palmer et al., WO 01/68645. Deprotection under standard conditions (Tet. Lett. 1992, 447-480) provided N-[(1S,2R)-2-({[cyano(cyclopropyl) methyl]amino}carbonxyl)cyclohexyl]-4-[2-(piperidin-4-ylamino)-1,3-thiazol-4-yl]benzamide trifluoroacetate.

Additional compounds prepared by the above method are shown in Table 1.

Example 4

Example of Method D

Synthesis of N-[(1S,2R)-2-({[(1S)-1-cyano-3-methylbutyl]amino}carbonyl)cyclohexyl]-4-(1H-1,2,4-triazol-1-yl)benzamide

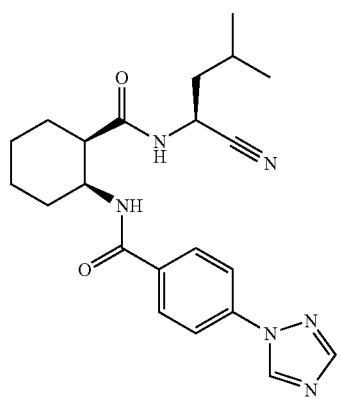

Step 1

(2-Acetyl-cyclohexyl)-carbamic acid benzyl ester

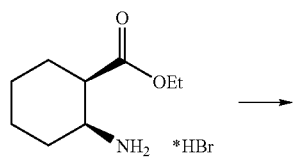

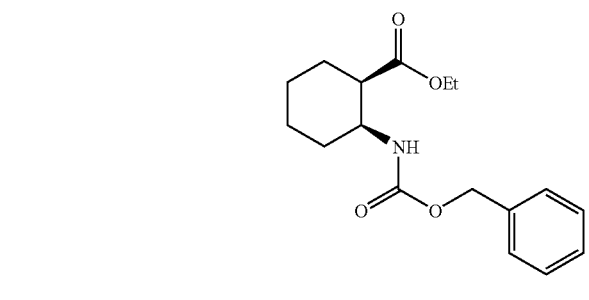

To a 0° C. solution of ethyl cis-2-amino-1-cyclohexanecarboxylate HBr salt (22.34 g, 88.6 mmol) in 250 mL of methylene chloride, was added benzyl chloroformate (12.6 mL, 88.3 mmol) and 250 mL of an aqueous sodium carbonate solution. The reaction mixture was stirred for 24 h at ambient temperature. The organic layer was separated and washed with 250 mL of water, dried over sodium sulfate, filtered and concentrated to give a crude liquid. The product was purified by column chromatography (10-50:90-50 ethyl acetate/hexanes) to give 26.45 g of (2-acetyl-cyclohexyl)-carbamic acid benzyl ester as a clear liquid. Yield: 98%, MS: 306 (M+H$^+$).

Step 2

2-Benzyloxycarbonylamino-cyclohexanecarboxylic acid

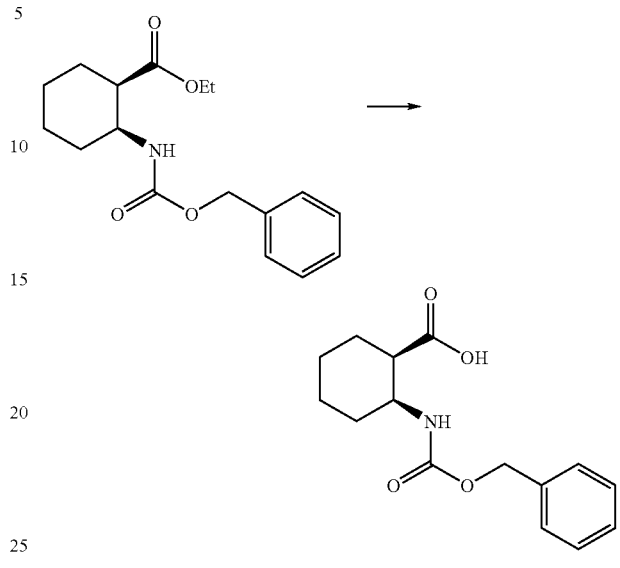

The ester of step 1 (26.45 g, 86.62 mmol) was dissolved in 250 mL of tetrahydrofuran and treated with a solution of lithium hydroxide monohydrate (10.65 g, 256 mmol) in 250 mL of water and stirred at ambient temperature for 24 h. The reaction mixture was cooled to 0° C. and neutralized with 300 mL of a 1N HCl solution. Ethyl acetate (400 mL) was added and the organic layer was separated, dried over sodium sulfate, filtered and concentrated to give a crude solid. The product was purified by recrystallizing from ethyl acetate/hexanes to give 19.60 g of a white solid. Yield: 82%, MS: 278 (M+H$^+$), mp=120.1-123.1° C.

Step 3

[2-(1-Carbamoyl-3-methyl-butylcarbamoyl)-cyclohexyl]-carbamic acid benzyl ester

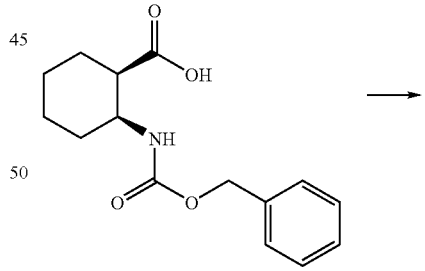

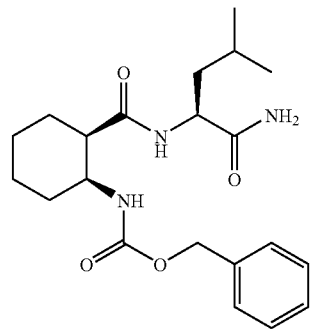

To a solution of the carboxylic acid of step 2 (10.2 g, 36.9 mmol), L-Leucineamide hydrochloride (6.18 g, 40.5 mmol), EDCI hydrochloride (5.48 g, 40.6 mmol), and HOBT (5.48 g, 40.6 mmol) in 100 mL of anhydrous DMF, was added N-methylmorpholine (12.0 mL, 109 mmol). The reaction mixture was stirred at ambient temperature for 24 h, then added 300 mL of water and 400 mL of ethyl acetate. The organic layer was separated and washed with two 300 mL portions of a 0.5 M HCl solution, 300 mL of water, then dried over sodium sulfate, filtered and recrystallized from ethyl acetate/hexanes to give 13.2 g of [2-(1-Carbamoyl-3-methyl-butylcarbamoyl)-cyclohexyl]-carbamic acid benzyl ester as a white solid. Yield: 92%, MS: 412 (M+Na$^+$), mp=188.0-189.5° C.

Step 4

[2-(1-Cyano-3-methyl-butylcarbamoyl)-cyclohexyl]-carbamic acid benzyl ester

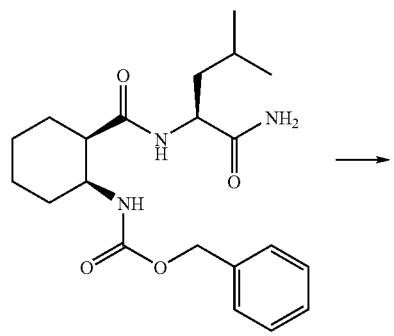

To a 0° C. solution of the amide of step 3 (13.2 g, 33.9 mmol) in 150 mL of anhydrous pyridine was added trifluoroacetic anhydride (5.50 mL, 38.9 mmol) dropwise slowly over a 3 min period. The reaction mixture was stirred for 15 min and then poured into a slurry of ice and 1N HCl solution. The mixture was extracted with 500 mL of ethyl acetate, and washed with three 400 mL portions of 1N HCl, 400 mL of water, dried over sodium sulfate, filtered and concentrated to give a crude solid. Recrystallization from ethyl acetate/hexanes gave 11.3 g of [2-(1-Cyano-3-methyl-butylcarbamoyl)-cyclohexyl]-carbamic acid benzyl ester as a white solid. Yield: 90%, MS: 394 (M+Na$^+$), mp=103.6-106.5° C.

Step 5

2-Amino-cyclohexanecarboxylic acid (1-cyano-3-methyl-butyl)-amide

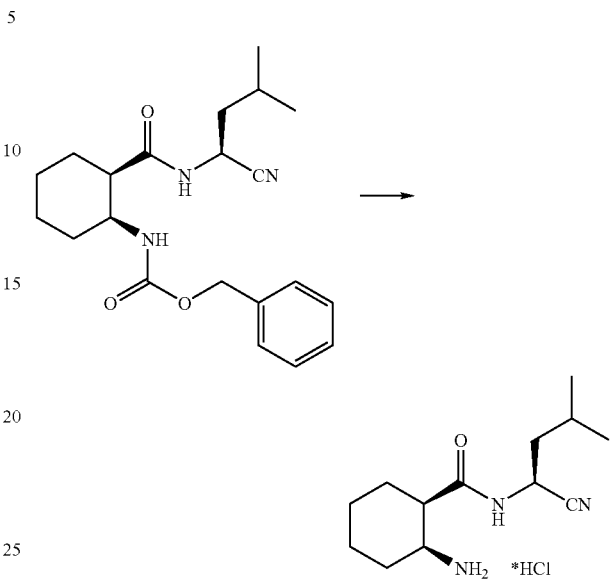

A solution of the carbamate of step 4 (11.3 g, 30.4 mmol) and palladium on activated carbon (1.0 g, 10% by wt.) in 250 mL of ethyl acetate was stirred for 24 h under a hydrogen atmosphere. The reaction mixture was filtered through a pad of celite, concentrated, then treated with a 1N solution of HCl in ether (35 mL). The resulting suspension was filtered and dried to give a 5.96 g of the hydrochloride salt of 2-Amino-cyclohexanecarboxylic acid (1-cyano-3-methyl-butyl)-amide as a white hygroscopic powder. Yield: 72%, MS: 238 (M+H$^+$), mp=133.3-135.0° C.

Step 6

N-[(1S,2R)-2-({[(1S)-1-cyano-3-methylbutyl]amino}carbonyl)cyclohexyl]-4-(1H-1,2,4-triazol-1-yl)benzamide

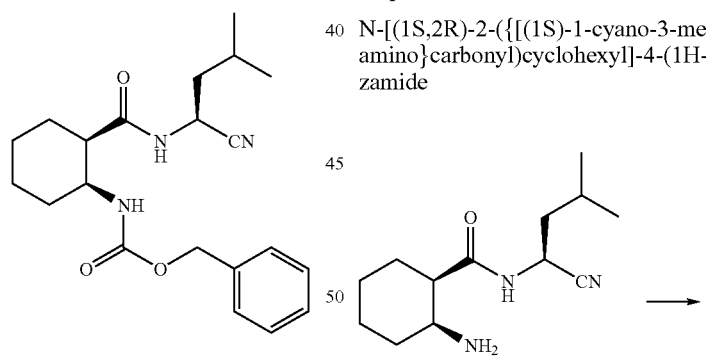

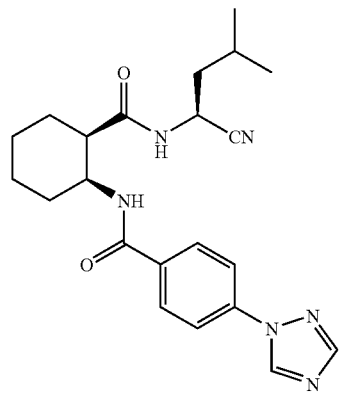

To a solution of the amine (157 mg, 0.66 mmol), 4-(1H-1,2,4-triazol-1-yl)benzoic acid (132 mg, 0.69 mmol), EDCI hydrochloride (145 mg, 0.76 mmol), HOBT (106 mg, 0.78 mmol) in 6.0 mL of DMF was added N-methylmorpholine (0.15 mL, 1.36 mmol) and stirred at ambient temperature for 24 h. The reaction mixture was partitioned between 50 mL of water and 50 mL of ethyl acetate. The organic layer was washed with two 50 mL portions of 1N HCl solution, 50 mL of water, dried over sodium sulfate, filtered, concentrated and purified by column chromatography (methanol/methylene chloride, 3:97) to give 170 mg of N-[(1S,2R)-2-({[(1S)-1-cyano-3-methylbutyl]amino}carbonyl)cyclohexyl]-4-(1H-1,2,4-triazol-1-yl)benzamide as a white solid. Yield: 63%, MS: 409 (M+H$^+$), mp=156.0-158.9° C.

Additional compounds prepared by the above method are shown in Table 1.

Example 5

Example of Method E

Synthesis of 4-chloro-N-[2-({[(1S)-1-cyano-2-thien-3-ylethyl]amino}carbonyl)cyclohexyl]benzamide

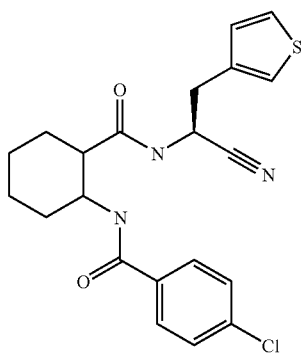

To 5.033 g of 9H-fluoren-9-ylmethoxy-2,4-dimethoxyphenyl(4-hydroxybenzyl) carbamate Rink polystyrene resin in a large glass bubbler was added 20% piperidine/DMF (80 mL). The reaction was bubbled with nitrogen for 30 minutes, filtered, and washed three times with 80 mL of CH$_2$Cl$_2$, once with MeOH and again with CH$_2$Cl$_2$. To the resin suspended in NMP, 3 eq EDCI (1.8 g), 1 eq. (0.42 g), HOBT, 9 eq (3.1 mL) NMP and 3 eq (3.7 g) FMOC-3-thienylAla were added, and the resin was bubbled with nitrogen overnight. The reaction was filtered and washed 3 times with 80 mL with CH$_2$Cl$_2$ then with MeOH and again with CH$_2$Cl$_2$. To the resin was added 80 mL of 20% piperidine/DMF. The reaction was bubbled with nitrogen for 30 min, filtered and washed three times with 80 mL of CH$_2$Cl$_2$, then with MeOH and again with CH$_2$Cl$_2$. To the resin was added 3 eq EDCI (1.8 g), 1 eq. (0.42 g), HOBT, 9 eq (3.1 mL) NMP and 3 eq (3.4 g) FMOC-cyclohexanecarboxylic acid. The resin was then suspended in NMP (80 mL) and bubbled overnight. The reaction was then filtered and washed three times with 80 mL of CH$_2$Cl$_2$, once with MeOH and again with CH$_2$Cl$_2$ and allowed to dry in a vacuum dessicator.

To 250 mg of this resin in a solid phase extraction vial was added 20% piperidine/DMF (2.5 mL). The reaction was allowed to sit for 30 minutes, filtered and washed three times with 4 mL with CH$_2$Cl$_2$, once with MeOH and again with CH$_2$Cl$_2$. To the resin was added 3 eq DIC (49 uL), 0.05 eq. DMAP (49 uL of a 0.116 M soln in THF), and 3 eq. 4-chlorobenzoic acid (49 mg). The resin was then suspended in CH$_2$Cl$_2$ (2.5 mL) and rotated overnight. The reaction was then filtered and washed three times with 4 mL of CH$_2$Cl$_2$, once with MeOH and again with CH$_2$Cl$_2$. The resin was then treated with 10% TFA/CH$_2$Cl$_2$ (2.5 ml) for 30 min, filtered and washed twice with 2.5 mL of CH$_2$Cl$_2$. The filtrate was evaporated on a Speed-Vac and dissolved in CH$_2$Cl$_2$ (2.5 mL). Burgess reagent (2 eq, 50 mg) was added and the reaction stirred overnight. The reaction was then evaporated on a Speed-Vac and purified by reverse phase high pressure liquid chromatography to yield 3.7 mg of 4-chloro-N-[2-({[(1S)-1-cyano-2-thien-3-ylethyl]amino}carbonyl)cyclohexyl]benzamide as a 92% pure sample.

Additional compounds prepared by the above method are shown in Table 1.

Example 6

Inhibitory Activity of the Compounds of the Invention Against Cathepsin K, S, L and B The inhibitory activity of the compounds against cathepsin K, S, L and B was tested at room temperature in 96-wells opaque white polystyrene plates (Costar). The cathepsin K inhibitory activity was tested as follows:

5 μl of an inhibitor diluted in 5 mM sodium phosphate, NaCl 15 mM pH 7.4 containing 1% DMSO (final concentrations: 10-0.0001 μM) were preincubated for 10 min with 35 μl of human recombinant cathepsin K (final concentration: 1 nM) diluted in assay buffer (100 mM sodium acetate pH 5.5 containing 5 mM EDTA and 20 mM cysteine). After addition of 10 μl of the fluorogenic substrate Z-Leu-Arg-MCA diluted in assay buffer (final concentration: 5 μM), increase of fluorescence (excitation at 390 nm and emission at 460 nm) was measured for 7.5 min every 45 sec. The initial velocity (RFU/min) was derived from the linear fit of the 11 reading points.

The cathepsin B inhibitory activity was assayed under the same conditions as the cathepsin K inhibitory activity using human liver cathepsin B (Calbiochem) at a final concentration of 1 nM.

The cathepsin L inhibitory activity was assayed under the same conditions as the cathepsin K inhibitory activity using human liver cathepsin L (Calbiochem) at a final concentration of 3 nM.

Cathepsin S inhibitory activity was assayed analogously to the cathepsin K inhibitory activity, except that the buffer was 100 mM potassium phosphate, 5 mM EDTA, 5 mM DTT (freshly added), 0.01% Triton X-100, pH 6.5 and fluorogenic substrate was Z-Val-Val-Arg-MCA (Bachem) (final concentration: 20 μM). Human recombinant cathepsin S (Wiederanders et al., *Eur. J. Biochem.* 1997, 250, 745-750) was used at a final concentration of 0.5 nM.

Using the above assays, the compounds of the invention were found to selectively inhibit Cathepsin K.

Example 7

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
| --- | --- |
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
| --- | --- |
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
| --- | --- |
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
| --- | --- |
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
| --- | --- |
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
| --- | --- |
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula (I)

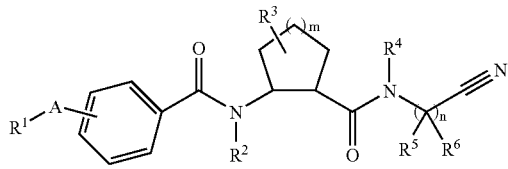

wherein:
m is from 1 to 3;
n is 1 or 2;
A is: —(CR$^a$R$^b$[[$_2$]])$_p$—; —O—(CR$^a$R$^b$[[$_2$]])$_s$—, —NR$^c$—(CR$^a$R$^b$[[$_2$]])$_t$—; or —CH=CH—;
wherein p and s each individually is from 0 to 3, t is from 1 to 3, and R$^a$, R$^b$ and R$^c$ each independently is hydrogen or alkyl;
R$^1$ is: heteroaryl selected from pyrolyl, thiazolyl, oxazolyl, thienyl, imidazolyl, triazolyl, furyl, pyridinyl, and pyrazolyl; heterocylcyl selected from morpholinyl, piperazinyl, piperidinyl, pyrrolidinyl, thiomorpholinyl, thiazinanyl, oxidothiomorpholinyl, dioxidothiomorpholinyl, oxidothiazinanyl, dioxidothiazinanyl, and 1,1,3-trioxidothiomorpholinyl; or —NR$^d$S(O)$_q$—R$^c$; wherein q is from 0 to 2, R$^d$ is hydrogen, alkyl or optionally substituted phenyl and R$^c$ is hydrogen, alkyl or pyridinylmethyl;
R$^2$, R$^3$, R$^4$ and R$^5$ each independently is hydrogen or alkyl; and
R$^6$ is hydrogen, alkyl, optionally substituted benzyl, thienylmethyl, pyridylmethyl, cycloalkyl, or —(CR$^f$R$^g$)$_r$S(O)$_q$—R$^h$ where R$^f$, R$^g$ and R$^h$ each independently is hydrogen or alkyl and r is 1 or 2;
and pharmaceutically acceptable salts thereof.

2. The compound of claim 1, wherein m is 2.

3. The compound of claim 2, wherein n is 1.

4. The compound of claim 3, wherein A is: —(CR$^a$R$^b$[[$_2$]])$_p$—.

5. The compound of claim 4, wherein p is 0.

6. The compound of claim 4, wherein R$^1$ is a heteroaryl selected from pyrolyl, thiazolyl, oxazolyl, thienyl, imidazolyl, triazolyl, furyl, pyridinyl, and pyrazolyl.

7. The compound of claim 6, wherein R$^1$ is selected from pyrrol-1-yl, 1,3-thiazol-4-yl, 1,3-thiazol-2-yl, 2-methyl-1,3-thiazol-4-yl, 2-(piperidin-4-yl-amino)-1,3-thiazol-4-yl, 2-[aminopiperidin-(1-carboxylate allyl ester)-4-yl]-1,3-thiazol-2-yl, 4-chloromethyl-1,3-thiazol-2-yl, 1,3-oxazol-5-yl, oxazol-4-yl, thien-2-yl, 5-bromothien-2-yl, 5-methylthien-2-yl, imidazol-1-yl, imidazol-5-yl, 1-methylimidazol-5-yl, 1-methylimidazol-2-yl, 1,2,4-triazolyl, 2-furyl, pyridin-3-yl, pyridin-2-yl, pyridin-4-yl, 6-methylpyridin-3-yl, 5-methylpyridin-3-yl, 6-methylpyridin-2-yl, pyrazol-5-yl, pyrazol-1-yl and methylpyrazol-3-yl.

8. The compound of claim 4, wherein R$^1$ is a heterocyclyl selected from from morpholinyl, piperazinyl, piperdinyl, pyrrolidinyl, thiomorpholinyl, thiazinanyl, oxidothiomorpholinyl, dioxidothiomorpholinyl, oxidothiazinanyl, dioxidothiazinanyl, and 1,1,3-trioxidothiomorpholinyl.

9. The compound of claim 8, wherein R$^1$ is piperidin-4-yl, pyrrolidin-1-yl, piperidin-(1-carboxylate allyl ester)-4-yl, morpholin-4-yl, piperazin-1-yl, 4-methylpiperazin-1-yl, 4-n-propylpiperazin-1-yl, 4-isopropylpiperazin-1-yl, 4-benzylpiperazin-1-yl, piperidin-1-yl, 1-n-propylpiperidin-4-yl, 1-ethylpiperidin-4-yl, 1-(2-methoxyethyl)piperidin-4-yl, 4-(1,1,4-trioxidothiomorpholin-4-yl), 4-(1,1-dioxide-1,2-thiazinan-2-yl and 4-(1,1-dioxidothiomorpholin-4-yl).

10. The compound of claim 5, wherein R$^1$ is —NR$^d$S(O)$_q$—R$^e$ and wherein R$^d$ is hydrogen, q is 2 and R$^e$ is methyl or 4-methylphenyl.

11. The compound of claim 4, wherein p is 1.

12. The compound of claim 11, wherein R$^1$ is a heteroaryl selected from pyrolyl, thiazolyl, oxazolyl, thienyl, imidazolyl, triazolyl, furyl, pyridinyl, and pyrazolyl.

13. The compound of claim 12, wherein R$^1$ is 5-methylpyridin-3-yl or imdazol-1-yl.

14. The compound of claim 4, wherein p is 2.

15. The compound of claim 14, wherein R$^1$ is a heteroaryl selected from pyrolyl, thiazolyl, oxazolyl, thienyl, imidazolyl, triazolyl, furyl, pyridinyl, and pyrazolyl.

16. The compound of claim 14, wherein R$^1$ is —NR$^d$S(O)$_q$—R$^e$ and wherein R$^d$ is hydrogen, q is 2 and R$^e$ is methyl.

17. The compound of claim 14, wherein R$^1$ is a heterocyclyl selected from morpholinyl, piperazinyl, piperidinyl, pyrrolidinyl, thiomorpholinyl, thiazinanyl, oxidothiomorpholinyl, dioxidothiomorpholinyl, oxidothiazinanyl, dioxidothiazinanyl, and 1,1,3-trioxidothiomorpholinyl.

18. The compound of claim 4, wherein p is 3.

19. The compound of claim 18, wherein R$^1$ is a heteroaryl selected from pyrolyl, thiazolyl, oxazolyl, thienyl, imidazolyl, triazolyl, furyl, pyridinyl, and pyrazolyl.

20. The compound of claim 19, wherein R$^1$ is pyridin-3-yl, pyridin-4-yl, or imidazol-1-yl.

21. The compound of claim 1, wherein A is —O—(CR$^a$R$^b$[[$_2$]])$_s$—.

22. The compound of claim 21, wherein s is 0.

23. The compound of claim 22, wherein R$^1$ is a heteroaryl selected from pyrolyl, thiazolyl, oxazolyl, thienyl, imidazolyl, triazolyl, furyl, pyridinyl, and pyrazolyl.

24. The compound of claim 23, wherein R$^1$ is 4-methylpyridin-3-yl.

25. The compound of claim 21, wherein s is 2.

26. The compound of claim 25, wherein R$^1$ is a heteroaryl selected from pyrolyl, thiazolyl, oxazolyl, thienyl, imidazolyl, triazolyl, furyl, pyridinyl, and pyrazolyl.

27. The compound of claim 26, wherein R$^1$ is pyridin-2-yl, pyridin-3-yl, pyridin-4-yl, pyrrol-1-yl, or imidazol-1-yl.

28. The compound of claim 25, wherein R$^1$ is a heterocyclyl selected from morpholinyl, piperazinyl, piperdinyl, pyrrolidinyl, thiomorpholinyl, thiazinanyl, oxidothiomorpholinyl, dioxidothiomorpholinyl, oxidothiazinanyl, dioxidothiazinanyl, and 1,1,3-trioxidothiomorpholinyl.

29. The compound of claim 28, wherein R$^1$ is morpholin-4-yl, piperazin-1-yl, piperazin-1-yl, and 4-methylpiperazin-1-yl.

30. The compound of claim 21, wherein s is 3.

31. The compound of claim 30, wherein R$^1$ is a heteroaryl selected from pyrolyl, thiazolyl, oxazolyl, thienyl, imidazolyl, triazolyl, furyl, pyridinyl, and pyrazolyl.

32. The compound of claim 31, wherein R$^1$ is pyridin-4-yl, pyridin-3-yl, or pyridine-2-yl.

33. The compound of claim 5, wherein R$^1$ is —NR$^d$S(O)$_q$—R$^e$ and wherein R$^d$ is hydrogen, q is 2 and R$^e$ is 4-pyridin-1-yl.

34. The compound of claim 1, wherein A is —NR$^c$—(CR$^a$R$^b$[[$_2$]])$_t$—.

35. The compound of claim 34, wherein t is 1.

36. The compound of claim 35, wherein R$^1$ is a heteroaryl selected from pyrolyl, thiazolyl, oxazolyl, thienyl, imidazolyl, triazolyl, furyl, pyridinyl, and pyrazolyl.

37. The compound of claim 36, wherein $R^1$ is pyridin-3-yl, 5-methylthien-2-yl, 1,3-thiazol-2-yl, pyrazol-1-yl, 2-furyl, imidazol-1-yl and 1-methylimidazol-2-yl.

38. The compound of claim 34, wherein t is 2.

39. The compound of claim 38, wherein $R^1$ is a heteroaryl selected from pyrolyl, thiazolyl, oxazolyl, thienyl, imidazolyl, triazolyl, furyl, pyridinyl, and pyrazolyl.

40. The compound of claim 38, wherein $R^1$ is a heterocyclyl selected from morpholinyl, piperazinyl, piperdinyl, pyrrolidinyl, thiomorpholinyl, thiazinanyl, oxidothiomorpholinyl, dioxidothiomorpholinyl, oxidothiazinanyl, dioxidothiazinanyl, and 1,1,3-trioxidothiomorpholinyl.

41. The compound of claim 40, wherein $R^1$ is morpholin-4-yl.

42. The compound of claim 34, wherein t is 3.

43. The compound of claim 42 wherein $R^1$ is pyridin-3-yl, 5-methylthien-2-yl, 1,3-thiazol-2-yl, pyrazol-1-yl, 2-furyl, imidazol-1-yl and 1-methylimidazol-2-yl.

44. The compound of claim 42, wherein $R^1$ is a heterocyclyl selected from morpholinyl, piperazinyl, piperdinyl, pyrrolidinyl, thiomorpholinyl, thiazinanyl, oxidothiomorpholinyl, dioxidothiomorpholinyl, oxidothiazinanyl, dioxidothiazinanyl, and 1,1,3-trioxidothiomorpholinyl.

45. The compound of claim 1, wherein A is —CH═CH—.

46. The compound of claim 45, wherein $R^1$ is a heteroaryl selected from pyrolyl, thiazolyl, oxazolyl, thienyl, imidazolyl, triazolyl, furyl, pyridinyl, and pyrazolyl.

47. The compound of claim 45, wherein $R^1$ is pyridin-4-yl.

48. The compound of claim 1, wherein $R^6$ is alkyl.

49. The compound of claim 48, wherein $R^6$ is isobutyl.

50. The compound of claim 1, wherein $R^6$ is thienylmethyl.

51. The compound of claim 50, wherein $R^6$ is thien-3-ylmethyl.

52. The compound of claim 1, wherein $R^6$ is cycloalkyl.

53. The compound of claim 52, wherein $R^6$ is cyclopropyl.

54. The compound of claim 1, wherein $R^6$ is —$(CR^fR^g)_t$ $S(O)_q$—$R^h$.

55. The compound of claim 54, wherein $R^f$ and $R^g$ are hydrogen, and $R^h$ is alkyl.

56. The compound of claim 55, wherein r is 1, q is 0 and $R^h$ is ethyl.

57. The compound of claim 55, wherein r is 2, q is 2 and $R^h$ is methyl.

58. The compound of claim 1, wherein $R^6$ is optionally substituted benzyl.

59. The compound of claim 58, wherein $R^6$ is 2,3-diflurobenzyl.

60. The compound of claim 58, wherein $R^6$ is 4-nitrobenzyl.

61. A compound of claim 1, wherein said compound is of the formula (II):

(II)

and wherein A, $R^1$ and $R^6$ are defined in claim 1.

62. The compound of claim 1, wherein said compound is of the formula (II):

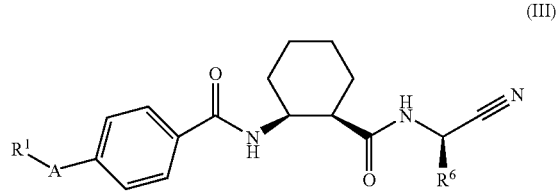

(III)

and wherein A, $R^1$ and $R^6$ are defined in claim 1.

63. A compound of claim 1, wherein said compound is selected from:

N-[(1S,2R)-2-({[cyano(cyclopropyl) methyl]amino}carbonyl)cyclohexyl]-4-(1H-pyrrol-1-yl)benzamide;

Allyl 4-({4-[4-({[(1S,2R)-2-({[cyano(cyclopropyl)methyl]amino}carbonyl)cyclohexyl]amino}carbonyl)phenyl]-1,3-thiazol-2-yl}amino) piperidine-1-carboxylate;

N-[(1S,2R)-2-({[cyano(cyclopropyl) methyl]amino}carbonyl)cyclohexyl]-4-[2-(piperidine-4-ylamino)-1,3-thiazol-4-yl]benzamide trifluoroacetate;

N-((1S,2R)-2-{[(cyanomethyl)amino]carbonyl}cyclohexyl)-4-(2-morpholin-4-ylethoxy)benzamide;

N-[(1S,2R)-2-({[(S)-cyano(cyclopropyl)methyl]amino}carbonyl)cyclohexyl]-4-(2-morpholin-4-ylethoxy)benzamide;

N-[(1S,2R)-2-({[(S)-cyano(cyclopropyl)methyl]amino}carbonyl)cyclohexyl]-4-(1,3-oxazol-5-yl)benzamide;

4-[4-(chloromethyl)-1,3-thiazol-2-yl]-N-((1S,2R)-2-{[(cyanomethyl) amino]carbonyl}cyclohexyl) benzamide;

N-((1S,2R)-2-{[(cyanomethyl)amino]carbonyl} cyclohexyl)-4-(4-methylpiperazin-1-yl)benzamide;

N-((1S,2R)-2-{[(cyanomethyl)amino]carbonyl} cyclohexyl)-4-(1H-pyrrol-1-yl)benzamide;

N-((1S,2R)-2-{[(cyanomethyl)amino]carbonyl} cyclohexyl)-4-thien-2-ylbenzamide;

N-((1S,2R)-2-{[(cyanomethyl)amino]carbonyl} cyclohexyl)-4-(4-propylpiperazin-1-yl)benzamide;

N-[(1S,2R)-2-({[(1S)-1-cyano-3-methylbutyl]amino}carbonyl) cyclohexyl]-4-(4-propylpiperazin-1-yl)benzamide;

N-((1S,2R)-2-{[(cyanomethyl)amino]carbonyl} cyclohexyl)-4-(4-isopropylpiperazin-1-yl)benzamide;

N-[(1S,2R)-2-({[(1S)-1-cyano-3-methylbutyl]amino}carbonyl) cyclohexyl]-4-(4-isopropylpiperazin-1-yl)benzamide;

N-((1S,2R)-2-{[(cyanomethyl)amino]carbonyl} cyclohexyl)-4-(1H-imidazol-1-yl)benzamide;

N-[(1S,2R)-2-({[(1S)-1-cyano-3-methylbutyl]amino}carbonyl) cyclohexyl]-4-(1,3-oxazol-4-yl)benzamide;

4-(5-bromothien-2-yl)-N-((1S,2R)-2-{[(cyanomethyl)amino]carbonyl} cyclohexyl)benzamide;

N-[(1S,2R)-2-({[(1S)-1-cyano-3-methylbutyl]amino{carbonyl) cyclohexyl]-4-(1H-1,2,4-triazol-1-yl) benzamide;

N-[(1S,2R)-2-({[(1S)-1-cyano-3-methylbutyl]amino{carbonyl) cyclohexyl]-4-(4-methylpiperazin-1-yl)benzamide;

N-((1S,2R)-2-{[(cyanomethyl)amino]carbonyl} cyclohexyl)-4-(1-propylpiperidin-4-yl)benazamide;
N-((1S,2R)-2-{[(cyanomethyl)amino]carbonyl} cyclohexyl)-4-(1-ethylpiperidin-4-yl)benazamide;
4-(4-benzylpiperazin-1-yl)-N-((1S,2R)-2-{[(cyanomethyl)amino]carbonyl}cyclohexyl)benzamide;
4-(5-bromothien-2-yl)-N-[(1S,2R)-2-({[(1S)-cyano3-methylbutyl]amino}carbonyl) cyclohexyl]benzamide;
N-((1S,2R)-2-{[(cyanomethyl)amino]carbonyl} cyclohexyl)-4-(2-furyl)benazamide;
N-[(1S,2R)-2-({[(1S)-1-cyano-3-methylbutyl]amino{carbonyl) cyclohexyl]-4-(pyridin-3-ylbenzamide;
N-[(1S,2R)-2-({[(1S)-1-cyano-3-methylbutyl]amino{carbonyl) cyclohexyl]-4-(6-methylpyridin-2-yl)benzamide;
N-((1S,2R)-2-{[(cyanomethyl)amino]carbonyl} cyclohexyl)-4-(1-methyl-1H-imidazol-5-yl)benazamide;
N-((1S,2R)-2-{[(cyanomethyl)amino]carbonyl} cyclohexyl)-4-[(methylsulfonyl)amino]benazamide;
N-[(1S,2R)-2-({[(1S)-1-cyano-3-methylbutyl]amino{carbonyl) cyclohexyl]-4-(2-morpholin-4-ylethoxy)benzamide;
N-[(1S,2R)-2-({[(1S)-1-cyano-3-methylbutyl]amino{carbonyl) cyclohexyl]-4-(2-piperidin-1-ylethoxy)benzamide;
N-[(1S,2R)-2-({[(1S)-1-cyano-3-methylbutyl]amino{carbonyl) cyclohexyl]-4-[(2-morpholin-4-ylethyl)amino]benzamide;
N-[(1S,2R)-2-({[(1S)-1-cyano-3-methylbutyl]amino{carbonyl) cyclohexyl]-4-[(2-methyl-1,3-thiazol-4-yl)benzamide;
N-[(1S,2R)-2-({[(1S)-1-cyano-3-methylbutyl]amino{carbonyl) cyclohexyl]-4-[1-(2-methoxyethyl) piperidin-4-yl]benzamide;
N-[(1S,2R)-2-({[(1S)-1-cyano-3-methylbutyl]amino{carbonyl) cyclohexyl]-4-(2-pyridin-2-ylethoxy)benzamide;
N-((1S,2R)-2-{[(cyanomethyl)amino]carbonyl{ cyclohexyl)-4-[1-(2-methyoxyethyl) piperidin-4-yl]benzamide;
N-[(1S,2R)-2-({[(1S)-1-cyano-3-methylbutyl]amino{carbonyl) cyclohexyl]-4-{[(4-methylphenyl)sulfonyl]amino}benzamide;
N-[(1S,2R)-2-({[(1S)-1-cyano-3-methylbutyl]amino{carbonyl) cyclohexyl]-4-[(6-methylpyridin-3-yl)oxy]benzamide;
N-[(1S,2R)-2-({[(1S)-1-cyano-3-methylbutyl]amino{carbonyl) cyclohexyl]-4-[(5-methylpyridin-3-yl)methyl]benzamide;
N-[(1S,2R)-2-({[(1S)-1-cyano-3-methylbutyl]amino{carbonyl) cyclohexyl]-4-[2-(4-methylpiperazin-1-yl)ethoxy]benzamide;
N-[(1S,2R)-2-({[(1S)-1-cyano-3-methylbutyl]amino{carbonyl) cyclohexyl]-4-(2-pyridin-4-ylethoxy) benzamide;
N-[(1S,2R)-2-({[(1S)-1-cyano-3-methylbutyl]amino{carbonyl) cyclohexyl]-4-(3-pyridin-4-ylpropoxy)benzamide;
N-[(1S,2R)-2-({[(1S)-1-cyano-3-methylbutyl]amino{carbonyl) cyclohexyl]-4-[2-1H-pyrrol-1-yl) ethoxy]benzamide;
N-((1S,2R)-2-{[(cyanomethyl)amino]carbonyl{ cyclohexyl)-4-(1H-pyrazol-5-yl)benzamide;
N-[(1S,2R)-2-({[(1S)-1-cyano-3-methylbutyl]amino{carbonyl) cyclohexyl]-4-(3-pyridin-3-ylpropoxy)benzamide;
N-((1S,2R)-2-{[(cyanomethyl)amino]carbonyl{ cyclohexyl)-4-(3-pyridine-4-ylpropoxy)benzamide;
N-[(1S,2R)-2-({[(1S)-1-cyano-3-methylbutyl]amino{carbonyl) cyclohexyl]-4-(1H-pyrazol-5-yl)benzamide;
N-[(1S,2R)-2-({[(1S)-1-cyano-3-methylbutyl]amino{carbonyl) cyclohexyl]-4-[(pyridin-3-ylmethyl)amino]benzamide;
N-((1S,2R)-2-{[(cyanomethyl)amino]carbonyl{ cyclohexyl)-4-{[(5-methylthien-2-yl)methyl]amino}benzamide;
N-[(1S,2R)-2-({[(1S)-1-cyano-3-methylbutyl]amino{carbonyl) cyclohexyl]-4-(3-pyridin-3-ylpropyl)benzamide;
N-((1S,2R)-2-{[(cyanomethyl)amino]carbonyl{ cyclohexyl)-4-[(1,3-thiazol-2-ylmethyl)amino]benzamide;
N-[(1S,2R)-2-({[(1S)-1-cyano-3-methylbutyl]amino{carbonyl) cyclohexyl]-4-(1-methyl-1H-pyrazol-3-yl)benzamide;
N-((1S,2R)-2-{[(cyanomethyl)amino]carbonyl{ cyclohexyl)-4-[(1H-pyrazol-1-ylmethyl)amino]benzamide;
N-((1S,2R)-2-{[(cyanomethyl)amino]carbonyl{ cyclohexyl)-4-(3-pyridin-4-ylpropyl)benzamide;
N-[(1S,2R)-2-({[(1S)-1-cyano-3-methylbutyl]amino{carbonyl) cyclohexyl]-4-(3-pyridin-4-ylpropyl) benzamide;
N-[(1S,2R)-2-({[(1S)-1-cyano-3-methylbutyl]amino{carbonyl) cyclohexyl]-4-[(2-furylmethyl)amino]benzamide;
N-[(1S,2R)-2-({[(1S)-1-cyano-3-methylbutyl]amino{carbonyl) cyclohexyl]-4-[2-(1H-imidazol-1-yl)ethoxy]benzamide;
N-[(1S,2R)-2-({[(1S)-1-cyano-3-methylbutyl]amino{carbonyl) cyclohexyl]-4-(1,1-dioxidothiomorpholin-4-yl)benzamide;
N-[(1S,2R)-2-({[(1S)-1-cyano-3-methylbutyl]amino{carbonyl) cyclohexyl]-4-(2-pyridinl-3-ylethoxy)benzamide;
N-[(1S,2R)-2-({[(1S)-1-cyano-3-methylbutyl]amino{carbonyl) cyclohexyl]-4-(1H-imidazol-1-ylmethyl)benzamide;
N-[(1S,2R)-2-({[(1S)-1-cyano-3-methylbutyl]amino{carbonyl) cyclohexyl]-4-thiomorpholin-4-ylbenzamide;
N-[(1S,2R)-2-({[(1S)-1-cyano-3-methylbutyl]amino{carbonyl) cyclohexyl]-4-(1,1-dioxio-1,2-thiazinan-2-yl)benzamide;
N-[(1S,2R)-2-({[(1S)-1-cyano-3-methylbutyl]amino{carbonyl) cyclohexyl]-4-(1,1,4-trioxidothiomorpholin-4-yl)benezamide;
N-[(1S,2R)-2-({[(1S)-1-cyano-3-methylbutyl]amino{carbonyl) cyclohexyl]-4-(1H-imidazol-1-yl)benzamide;
N-[(1S,2R)-2-({[(1S)-1-cyano-3-methylbutyl]amino{carbonyl) cyclohexyl]-4-[(2 -pyrrolidin-1-ylethyl)amino]benzamide;
N-[(1S,2R)-2-({[(1S)-1-cyano-3-methylbutyl]amino{carbonyl) cyclohexyl]-4-{[(1-methyl-1H-imidazol-2-yl)methyl]amino} benzamide;
N-[(1S,2R)-2-({[(1S)-1-cyano-3-methylbutyl]amino{carbonyl) cyclohexyl]-4-{2-[(methylsulfonyl)amino]ethyl}benzamide;
N-[(1S,2R)-2-({[(1S)-1-cyano-3-methylbutyl]amino{carbonyl) cyclohexyl]-4-[(E)-2-pyridin-4-ylethenyl]benzamide; and N-[(1S,2R)-2-({[(1S)-1-cyano-3-methylbutyl]amino}carbonyl) cyclohexyl]-4-[3-(1H-imidazol-1-yl)propyl]benzamide.

64. A pharmaceutical composition comprising a compound of claim 1 and a pharmaceutically acceptable carrier and/or adjuvant.

65. A pharmaceutical composition comprising a compound of claim 1 and a phosphonic acid or phosphonic ester selected from alendronic acid, cimadronic acid, clodronic acid, tiludronic acid, etidronic acid, ibandronic acid, risedronic acid, pyridronic acid, pamidronic acid, zolendronic acid, or a pharmaceutically acceptable salt or mixture thereof.

66. A method of preparing a compound of claim 1, comprising:

a) reacting a compound of formula (IV):

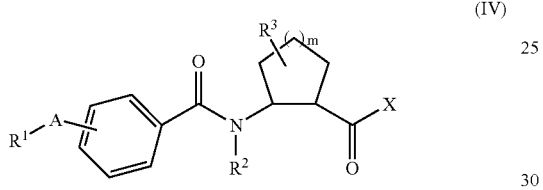

(IV)

wherein X is a leaving group and $R^1$, $R^2$, $R^3$, and A and m are defined in claim 1; with a compound of formula (V):

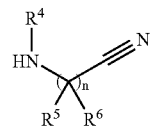

(V)

wherein $R^4$, $R^5$, $R^6$ and n are as defined in claim 1; or b) reacting a compound of formula (VI):

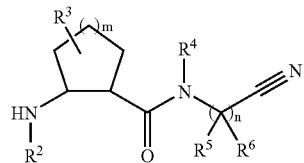

wherein $R^2$, $R^3$, $R^4$, $R^5$ and $R^6$ are as defined in claim 1, with a compound of formula (VII)

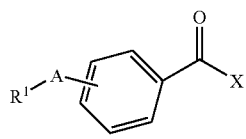

(VII)

wherein X is a leaving group and R1 and A are defined in claim 1; to provide a compound of formula (I).

* * * * *